(12) United States Patent
Apfel et al.

(10) Patent No.: US 12,312,631 B1
(45) Date of Patent: May 27, 2025

(54) HIGH-THROUGHPUT MULTIPLEXED SENSITIVITY AND RESISTANCE ASSAY

(71) Applicant: SAGEMEDIC CORPORATION, Redwood City, CA (US)

(72) Inventors: Christian Apfel, Redwood City, CA (US); Chiara Maestri, Redwood City, CA (US); Rajeshwar Nitiyanandan, Redwood City, CA (US); Parthasarathy Chandrakesan, Redwood City, CA (US); Ricardo Jerome Parker, Redwood City, CA (US)

(*) Notice: Subject to any disclaimer, the term of this patent is extended or adjusted under 35 U.S.C. 154(b) by 0 days.

(21) Appl. No.: 18/335,851

(22) Filed: Jun. 15, 2023

Related U.S. Application Data

(60) Provisional application No. 63/352,543, filed on Jun. 15, 2022.

(51) Int. Cl.
  *C12Q 1/06* (2006.01)
  *G01N 33/574* (2006.01)

(52) U.S. Cl.
  CPC ......... *C12Q 1/06* (2013.01); *G01N 33/57484* (2013.01); *C12Q 2304/80* (2013.01); *C12Q 2525/101* (2013.01); *C12Q 2525/117* (2013.01); *C12Q 2563/103* (2013.01)

(58) Field of Classification Search
  CPC ............................ C12Q 1/06; C12Q 2304/80; C12Q 2525/101; C12Q 2525/117; C12Q 2563/103; G01N 33/57484
  See application file for complete search history.

(56) References Cited

U.S. PATENT DOCUMENTS

| | | |
|---|---|---|
| 6,541,206 B1 | 4/2003 | Huszar |
| 7,083,911 B2 | 8/2006 | Wood et al. |
| 10,745,667 B2 | 8/2020 | Tang |
| 2014/0228246 A1 | 8/2014 | Rodgers et al. |

OTHER PUBLICATIONS

Sevin et al. (Cancer, 1993, vol. 71(4):1613-1620) (Year: 1993).*
Adan et al. (Current Pharmaceutical Biotechnology, 2016, 17, 1213-1221) (Year: 2016).*

(Continued)

*Primary Examiner* — Jeremy C Flinders
(74) *Attorney, Agent, or Firm* — Robert Brownstein

(57) ABSTRACT

In the clinic, most patients' cancer tissues have a heterogeneous histological appearance, often as a result of newly emerging and resistant cancer cell populations. Thus, viability tests to detect the sensitivity of a cancer tissue might not accurately predict a patient's tumor response if smaller but resistant cancer cells proliferate and replace the cells that are sensitive to the current treatment. Provided are methods to multiplex the detection of cell viability and proliferation in a single sample. A cell or tissue sample is treated, incubated with a glycosylamine, and subsequently washed. The sample is then permeabilized, and a first detectable marker is measured to quantify viability effects while a second detectable marker is measured to quantify proliferative effects. These methods may be used to more reliably predict treatment effects for a cancer patient and to evaluate a biological effect of a therapy on malignant viable cells.

16 Claims, 14 Drawing Sheets

(56) References Cited

OTHER PUBLICATIONS

Invitrogen (Click-iT® EdU Imaging Kit guide, 2011) (Year: 2011).*
Sigma-Aldrich (ATP Bioluminescence Kit Technical Bulletin, 2022) (Year: 2022).*
Chen, MiaoJuan et al., Science China Chemistry 54 (2011): 1702-1710 (Year: 2011).*
Elisia et al. (Phytochem. Anal., 2008, 19:479-486) (Year: 2008).*
DeLuca et al., "Factors affecting the kinetics of light emission from crude and purified firefly luciferase." Analytical Biochemistry 95(1), 194-198 (1979). DOI: 10.1016/0003-2697(79)90204-5. PMID: 495953.
Lomakina et al., "Bioluminescence Assay for Cell Viability", Biochemistry Moscow 80, 701-713, 2015, DOI: 10.1134/S0006297915060061.

* cited by examiner

|  | A549 | HCT-116 |
|---|---|---|
FIG. 5A
Cells
in Culture
Medium
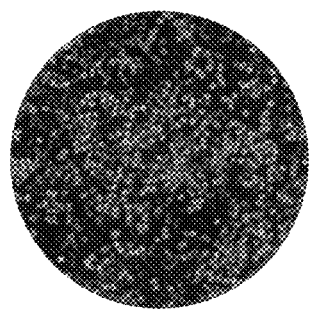
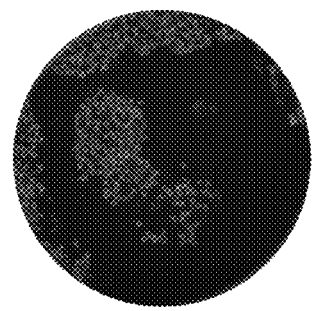
FIG. 5F
FIG. 5B
Cells
in Carrier
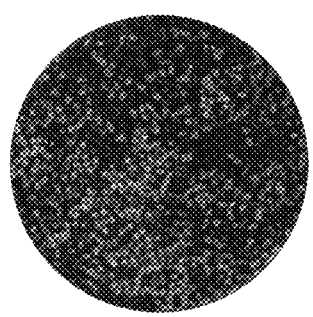
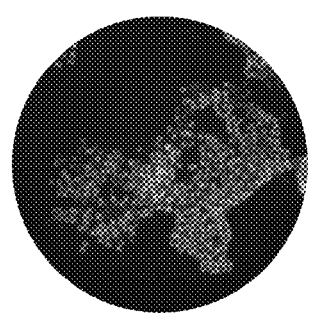
FIG. 5G
FIG. 5C
Low
Treatment
Concentration
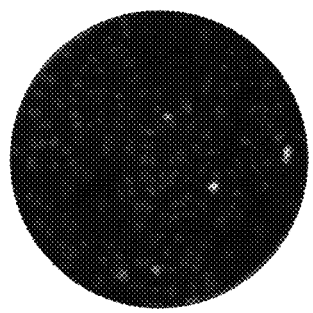
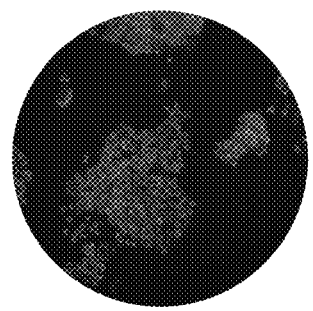
FIG. 5H
FIG. 5D
Medium
Treatment
Concentration
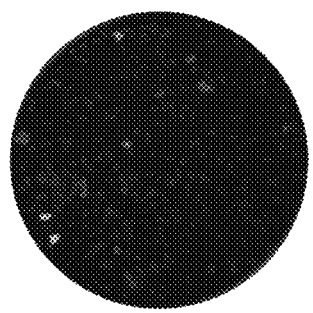
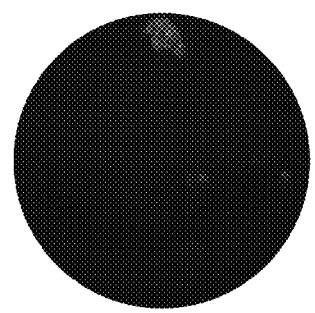
FIG. 5I
FIG. 5E
High
Treatment
Concentration
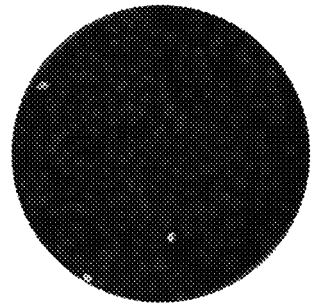
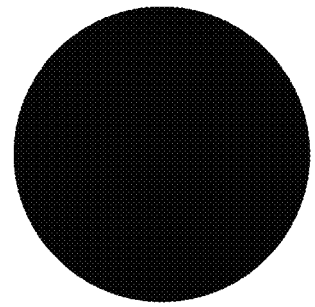
FIG. 5J
FIG. 5

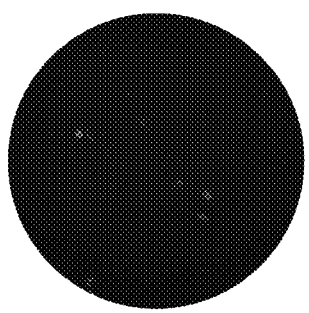
FIG. 6A
Cells in Culture Medium
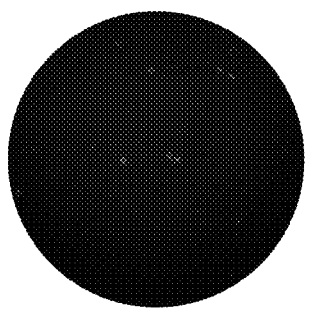
FIG. 6B
Cells in Carrier
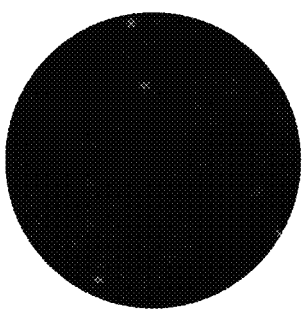
FIG. 6C
Low Treatment Concentration
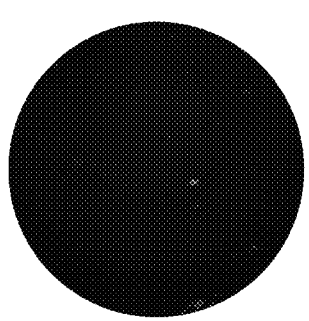
FIG. 6D
Medium Treatment Concentration
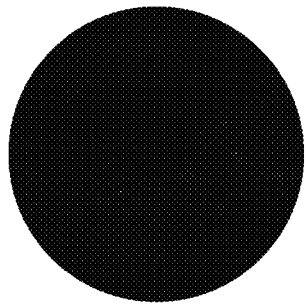
FIG. 6E
High Treatment Concentration
FIG. 6

FIG. 8C A549

FIG. 8D HCT-116

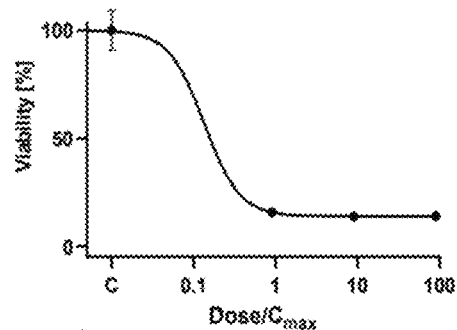
FIG. 9A
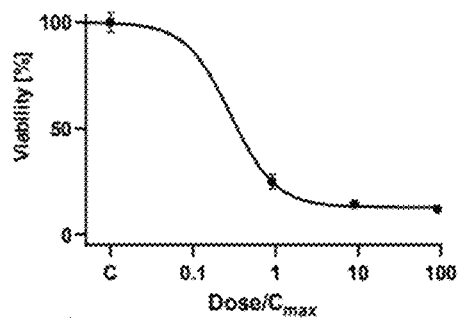
FIG. 9B
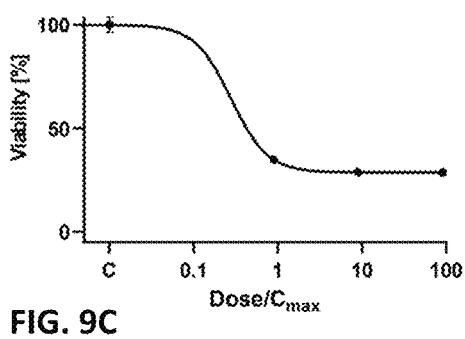
FIG. 9C
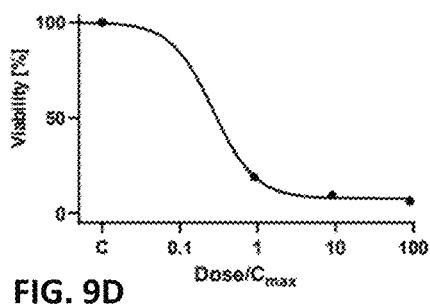
FIG. 9D
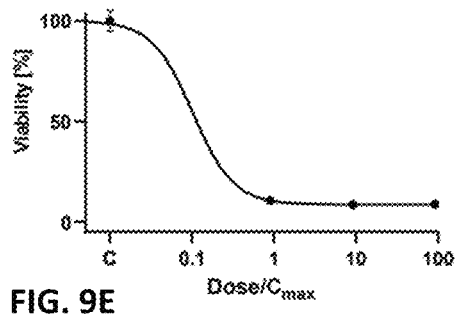
FIG. 9E
FIG. 9

HIGH-THROUGHPUT MULTIPLEXED SENSITIVITY AND RESISTANCE ASSAY

This application claims priority to and the benefit of U.S. Provisional Patent Application No. 63/352,543 filed Jun. 15, 2022, the entirety of which is herein incorporated for all purposes.

FIELD

The present teachings relate to multiplexed assay methods for treating and analyzing a diseased or malignant tissue or cell sample for cell viability and cell proliferation, for determining effective treatments, developing therapeutics, evaluating biological effects, and patient prognosis.

BACKGROUND

There are several methods to measure cell proliferation or cell viability. However, there is no high throughput method to multiplex the measurement of cell proliferation by quantifying DNA replication and the measurement of viability by quantifying ATP content on the same biological sample and within the same well of a multi-titer plate or reaction vial. Multiplexing a cell proliferation and a viability assay has clinical advantages. In contrast to cell line research, clinical biopsy samples tend to be heterogeneous, and it is often clinically relevant to know whether certain drugs affect proliferation, viability, or both. Clinical biopsy samples are also inherently small and multiplexing these tests will be more valuable for a clinician to consider various treatment options. These factors are particularly relevant too for examination of a fresh biopsy of a cancer patient, e.g., to understand whether certain treatment options might be effective in inhibiting further cancer growth, in shrinking or eliminating the cancer, or doing both, and to identify the most effective treatment in order to improve patient outcomes.

SUMMARY

In various embodiments, a multiplexed method is provided for detecting cell viability and cell proliferation. The multiplexed method includes detecting or measuring a first detectable marker to assess cell viability and detecting or measuring a second detectable marker to assess cell proliferation.

In various embodiments, the method can include treating and incubating cells with a glycosylamine. The method can include washing the treated cells followed by permeabilizing the cells. Permeabilizing can be by using a permeabilizing agent selected from the group comprising of Triton X-100, digitonin, viroporin, saponin, proteinase K, and combinations thereof. The method can include adding and measuring a first detectable marker to the permeabilized cells to quantify cell viability. The method can further include adding and measuring a second detectable marker to the permeabilized cells to quantify cell proliferation. In an alternative embodiment, washing can either follow treating and incubating the cells or be after measuring the first detectable marker.

In an additional embodiment, the multiplexed method can further comprise incubating the cells with a therapeutic agent, for example, for predicting a treatment effect, for example, for a patient's cancer. A reduction in cell viability can be a prediction of sensitivity of a patient's cancer to a therapeutic agent, e.g., a cytotoxic therapeutic agent, and uninhibited cell proliferation can be a prediction of resistance of the patient's cancer to a therapeutic agent, e.g. an anti-proliferative therapeutic agent.

In another embodiment, the multiplexed method can be used to evaluate a biological effect of a therapy on cells, e.g., cancer cells, malignant viable cells, by simultaneously detecting cell viability and cell proliferation. The multiplexed method can both treat and incubate the viable cells, and can do so with at least one therapeutic agent and a glycosylamine.

The method includes using a first detectable marker, e.g., a marker added to the permeabilized cells, to detect or measure, e.g. quantify, cell viability. The method includes using a second detectable marker, e.g., a marker added to the same permeabilized cells used to quantify cell viability, to detect or measure, e.g. quantify, cell proliferation. The detection or measurement of the first and second detectable markers can indicate at least one of reduced cell viability, for example, as a predictor of tumor sensitivity, and uninhibited cell proliferation, for example, as a predictor of tumor resistance of malignant cells. The detection or measurement of at least one of cell viability and proliferation can predict the effectiveness of therapy on malignant cells. The effectiveness can foretell one or more of patient prognosis, patient stratification, and efficacy of therapeutic treatments, including treatments in development.

In further embodiments, the permeabilized cells can be from one or more of: a benign tissue, a diseased tissue, an infected tissue, a solid cancer, a hematological cancer and/or combinations thereof. The permeabilized cells can be derived from a patient (e.g., from a patient's biopsy), the tumor of an animal model, or a cell culture (including a 2D or 3D cell culture). The permeabilized cells can be at least one of i) a tissue culture derived from a cancer biopsy from a patient or animal model; ii) a tissue culture derived from a non-cancerous biopsy from a patient or animal model; iii) a tissue culture derived from a cancer biopsy from a cancer patient or animal model undergoing treatment with the therapeutic agent; and iv) a tissue culture derived from a non-cancerous biopsy from a cancer patient or animal model undergoing treatment with a therapeutic agent.

In yet further embodiments, the cells to undergo permeabilization of the multiplexed method can be adherent in an extracellular matrix or fixed to a surface prior to permeabilization. The cells can be permeabilized with a permeabilizing agent such as Triton X100, digitonin, viroporin, saponin, proteinase K, and combinations thereof. Measuring a detectable marker can include detecting and/or measuring luminescence(s) and/or fluorescence(s) and can indicate the cell viability and cell proliferation, within the same cell culture. In still further embodiments, the first detectable marker for viability is a chemiluminescence marker, bioluminescence marker, fluorescent dye, fluorescent label, and/or radioactive label. Quantifying cell viability can comprise measuring cellular metabolic activity via the first detectable marker, wherein cellular metabolic activity is measured in a luminescent ATP assay.

In yet a further embodiment, quantifying cell proliferation can include detecting and/or measuring luminescence or fluorescence of the second detectable marker. Cell proliferation can be quantified, for example, by measuring a change in nucleic acid synthesis via said second detectable marker, for example, a second detectable marker selected from the group consisting of ethynyl-deoxyuracil (EdU), 5-bromo 2'-deoxyuridine (BrdU), 5-Vinyl-2'-deoxyuridine (VdU) and other similar molecular analogs. The second detectable marker can be incorporated into a molecule comprising at least one of a nucleoside(s), a nucleotide(s), a nucleoside analog, and a nucleotide analog. In a further embodiment, measuring or quantifying cell viability and/or cell proliferation can comprise measuring luminescence(s), fluorescence(s) and/or absorbance within the same cell culture. Luminescence, fluorescence and absorbance can be measured, for example, by flow cytometry, confocal microscopy, a plate reader, fluorescence imaging, spectroscopy, microscopy or combinations thereof.

In various embodiments, a kit for determining cell viability and cell proliferation is provided. The kit can be used to assess viability and proliferation within a single sample, for example, a single collective of cells obtained from a sample of cells or a sample of permeabilized cells residing within an assay reaction well of a multi-titer cell culture plate or a reaction vial. The kit can be used, for example, to predict treatment effects, for example, for a cancer patient, for example, for use in predicting effectiveness of a therapeutic agent and/or to evaluate a biological effect of a therapy, for example, on malignant viable cells. In various embodiments, the kit can be used to practice the various embodiments disclosed herein. The kit can include reagents. The reagents can include at least two detectable markers. The first detectable marker can be used to quantify cell viability, and the second detectable marker can be used to quantify cell proliferation, within the same culture. The detectable markers can include one or more of a dye, a fluorescent dye, a fluorescent label, a chemiluminescence marker, a bioluminescence marker, and a radioactive label.

INCORPORATION BY REFERENCE

All publications, references, patents, and patent applications mentioned in this document are herein incorporated by reference to the same extent as if each individual publication, reference, patent, or patent application was specifically and individually indicated to be incorporated by reference. In the event of inconsistent usages between this document and those documents so incorporated by reference, the usage in the incorporated reference should be considered supplementary to that of this document; for irreconcilable inconsistencies, the usage in this document controls.

Various features, aspects, and advantages of the present invention will become more apparent from the following detailed description of preferred embodiments of the invention, along with the accompanying drawings in which like numerals represent like components. Reference will now be made to various embodiments, examples of which are illustrated in the accompanying drawings.

BRIEF DESCRIPTION OF THE DRAWINGS

FIG. 5 shows SAGE EdU assay results for A549 (FIGS. 5A to 5E) and HCT-116 (FIGS. 5F to 5J) cell lines analyzed using the described methods, treated with each of three concentrations of a cellular treatment moiety (FIGS. 5C to 5E and FIGS. 5H to 5J) and compared with cell lines in cell culture medium (FIGS. 5A and 5F) and in carrier (FIGS. 5B and 5G) as viewed by confocal microscope (20×).

FIG. 6 shows SAGE EdU assay results for primary ovarian cancer cells analyzed using the described methods, treated with each of three concentrations of a cellular treatment or drug (FIGS. 6C to 6E) and compared with primary ovarian cancer cells in cell culture medium and in carrier (FIGS. 6A and 6B)

FIG. 9 depicts dose response curves of IC50 values for an ATP assay value using a cell-lysising based reagent (FIG. 9A), an ATP Assay on a multiplex plate (FIGS. 9B and 9C) and subsequent SAGE EdU Assay read by Plate Reader (FIG. 9D) and Confocal microscope (FIG. 9E).

DETAILED DESCRIPTION

Figure 1:
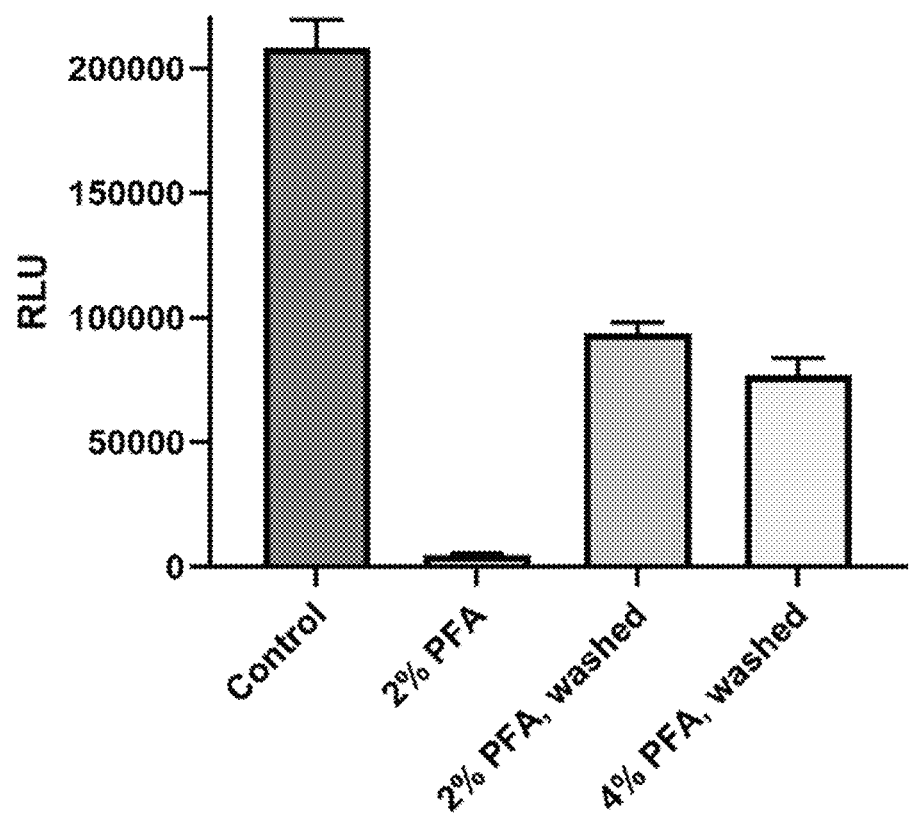
FIG. 1 is a bar graph depicting ATP measurements as relative luminescent units (RLUs) following cell fixation with varying percentages of paraformaldehyde (PFA), as described in Example 1.

Before the present compositions and methods are described, it is to be understood that the disclosed innovations are not limited to particular compositions, methods, kits or experimental conditions described, as such compositions, methods, kits and conditions may vary. It is also to be understood that the terminology used herein is for purposes of describing particular embodiments only, and is not intended to be limiting.

What is disclosed herein are various embodiments to reiterate the unique aspects of the disclosed in vitro methods for identifying in a cell, tissue, organ or organoid that has been cultured or grown in vitro, in situ and/or in vivo, both cell viability and proliferation in a single sample with an assay that detects multiple markers such as the described multiplex assay. The ability to detect cell viability and proliferation in a single sample can contribute to improved diagnosis, prognosis, and evaluation of treatment efficacy as well as contribute to personalized treatment design and therapy selection(s). The ability to do so within a single multiplex assay or protocol facilitates such assessments. The disclosed methods also find applications for assessing efficacy when developing therapeutic agents, evaluating a treatment, a therapy, a therapeutic agent, and broadly any type of treatment effect(s) by monitoring either the sensitivity or resistance as seen by reduced viability or proliferation, for example, in malignant cells undergoing a treatment or potential treatment regimen.

Unless defined otherwise, all technical and scientific terms used herein have the same meaning as commonly understood by one of ordinary skill in the art to which this invention belongs. As used herein, the recited terms have the following meanings. The following definitions are included to provide a clear and consistent understanding of the specification and claims. Any methods and materials similar or equivalent to those described herein can be used in the practice or testing of the disclosed invention, as it will be understood that modifications and variations are encompassed within the spirit and scope of the instant disclosure.

References in the specification to "one embodiment," "an embodiment," "another embodiment," "various embodiments," and the like, indicate that the described embodiment can include a particular aspect, feature, structure, moiety, or characteristic, but every embodiment may not necessarily include the particular aspect, feature, structure, moiety, or characteristic. Moreover, such phrases are not necessarily referring to the same embodiment. Further, when a particular aspect, feature, structure, moiety, or characteristic is described in connection with an embodiment, it is submitted that it is within the knowledge of one of ordinary skill in the art to effect or connect such aspect, feature, structure, moiety, or characteristic in connection with other embodiments whether or not explicitly described.

It is further noted that the claims may be drafted to exclude an optional element. As such, this statement is intended to serve as basis for the use of exclusive terminology, such as "solely," "only," "other than", and the like, in connection with any element described herein, and/or the recitation of claim elements or use of "negative" limitations.

The term "and/or" means any one of the items, any combination of the items, or all of the items with which this term is associated. The phrases "one or more" and "at least one" when read in context of its usage are readily understood by one of skill in the art, for example, the phrase can mean one, two, three, four, five, six, ten, 100, or any upper limit approximately 10, 100, or 1000 times higher than a recited lower limit.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range as if each numerical value and sub-range is explicitly recited. As a non-limiting example, each range discussed herein can be readily broken down into a lower third, middle third and upper third, as well as nested ranges within a larger range, etc. As will also be understood by one skilled in the art, all language such as "up to", "at least", "greater than", "less than", "more than", "or more", and the like, include the number recited and such terms refer to ranges that can be subsequently broken down into sub-ranges.

A range of values, for example, "1% to 5%" or "0.1% to 5%" should be interpreted to include not just 1% to 5%, but also the individual values (e.g., 1%, 2%, 3%, and 4%) and the sub-ranges (e.g., 0.1% to 0.5%, 1.1% to 2.2%, 3.3% to 4.4%) within the indicated range. Ranges may be expressed herein as from "about" or "approximately" one particular value to "about" or "approximately" another particular value. When such a range is expressed, another embodiment includes between each such pair of particular values. Similarly, when values are expressed as approximations by use of the antecedent "about" or "approximate" it will be understood that each particular value forms another embodiment. It is understood that the endpoints of each of the ranges are significant both in relation to the other endpoint and independently of the other endpoint. It is also understood that there are a number of values disclosed, wherein each value is also disclosed as "about" that particular value in addition to the value itself. For example, if the value "10" is disclosed, then "about 10" is also disclosed. It is also understood that when a value is disclosed that is "less than or equal to the value", or "greater than or equal to the value", possible ranges between these values are also disclosed, as appropriately understood by the person with ordinary skill in the art. For example, if the value "10" is disclosed the "less than or equal to 10" as well as "greater than or equal to 10" is also disclosed. Units, prefixes, and symbols are denoted in their Systeme International de Unites (SI) accepted form unless otherwise specified.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

For integer ranges, the term "about" can include one or two integers greater than and/or less than a recited integer at each end of the range and/or 20% more or less than the stated value. Unless indicated otherwise herein, the term "about" is intended to include values, e.g., ratios, mg/kg, weight percentages, proximate to the recited range that are equivalent in terms of the functionality of the individual ingredient, element, the composition, or the embodiment. The term "about" can also modify the end-points of a recited range as discuss above.

In this document, the terms "a," "an," or "the" are used to include one or more than one unless the context clearly dictates otherwise. Thus, for example, a reference to "a component" includes a plurality of such components, so that a component Z includes a plurality of components Z. Nouns used in the plural form, as used herein, can denote at least one or more than one of the noun. For example, the noun "marker" used in the plural form "markers" can include at least one marker or more than one marker.

The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods or processes described herein, the steps can be carried out in any order without departing from the principles of the invention, unless otherwise indicated herein or otherwise clearly contradicted by context, for example, when a temporal or operational sequence is explicitly recited.

Furthermore, specified steps can be carried out concurrently unless explicit claim language recites that they be carried out separately. For example, a claimed step of doing A and a claimed step of doing B can be conducted simultaneously within a single operation, and the resulting process will fall within the literal scope of the claimed process.

The following terms, as used herein, have the meanings ascribed to them unless specified otherwise.

As used herein, the term "biological effect" refers to any measurable biological response to a treatment, perturbation, condition, or the like, including, but not limited to, changes in cell cycle, cell proliferation, cell viability, cell death, apoptosis, etc. A "positive biological effect" refers to a response that is favorable, beneficial, helpful or the like, for example, a reduction of malignant viable cells when assayed for cell viability and/or reduced cell proliferation in the population of malignant viable cells. A "negative biological effect" refers to a response that is not favorable, not beneficial, not helpful or the like, for example, an increase or lack of reduction of malignant viable cells when assayed for cell viability and/or increased or lack of reduction of cell proliferation in the population of malignant viable cells.

As used herein, the terms "cell", "cells" and terms indicating either a homogenous or heterogeneous collection, culture or sample of cells is understood by the skilled artisan to refer to a plurality of cells, at least one or more cells and the like.

As used herein, the terms "cell culture," "tissue culture," "organ culture," and terms indicating other forms of in vitro cultivation of cells, tissues, spheroids, organoids and organs, can be used interchangeably to refer to the propagation of cells as entities or within the composition of a tissue, organoid or organ (any of which can be natural or synthetic, 3D-printed, donated or obtained from another genus or species). Thus and for example, use of the term "cell culture" without restriction also refers to any of the afore-referenced cultures though not explicitly stated as such. For example, the "cell culture" can be at least one of: neoplasm, a solid tumor culture, a liquid tumor culture, a diseased tissue, an infected tissue, a biopsy sample, an organ, an organoid and combinations thereof.

As used herein, the term "multiplex" refers to assay methods that are capable of assessing multiple biological effects, e.g. viability and proliferation, on cells, e.g., effects of a potential therapy on tumor cells in the same sample, as part of the same protocol though not necessarily at the exact same time. The sample can, for example, be in the same multi-titer well or vial and/or utilize the cells' supernatant transferred from a first multi-titer well or vial to a second multi-titer well or vial from the first assay to assess one or more additional biological effects in a second or more assay(s). More specifically, multiplex methods are disclosed that are capable of measuring at least a first and optionally a second detectable marker to quantify cell viability and cell proliferation, respectively, in a tissue culture, tumor sample, solid cancer, cell culture, malignant cell culture or research cell line.

As used herein, the terms "plural" and "plurality" can be used interchangeably and refer to two (2) or more of an item(s), thing(s) or entity(ies).

As used herein, the terms "proliferative," "proliferation" and "cell proliferation" can be used interchangeably and refers to an increase in cell number, for example, due to one or more cells undergoing reproduction or cell growth, or cell division and includes but is not limited to increase or exponential increase in the cell number. Cell proliferation can be described as both cell reproduction and cell division occurring simultaneously such that the mean number of cells is constant for a cell population. An increase in cell number can be described as tissue growth. Cancer can result from uncontrolled cell proliferation which can be seen as an increased cell proliferation rate or as a result of the cells failing to stop proliferation at a normal time.

As used herein, the phrase "Relative Luminescence Unit" ("RLU") refers to a unit for measuring the levels of adenosine triphosphate (ATP). The CellTiter-Glo® ATP Luminescent Cell Viability Assay (Catalog No. G9681, Promega Corp., Madison, WI), takes advantage of firefly luciferase's use of ATP to oxidize D-Luciferin and the resulting production of light in order to assess the amount of ATP.

The ATP assay is based on a reaction known as the firefly luciferase reaction catalyzed by the activity of the enzyme luciferase, which in presence of ATP, $Mg_2+$ and $O_2$ converts its substrate luciferin into oxyluciferin, emitting a luminescent signal at 562 nm (DeLuca, M., Wannlund, J., and McElroy, W. D. "Factors affecting the kinetics of light emission from crude and purified firefly luciferase." Analytical Biochemistry 95 (1), 194-198 (1979). DOI: 10.1016/0003-2697 (79) 90204-5. PMID: 495953). The luminescent signal is detected with the plate reader: For example, 1 ATP molecule corresponds to 1 RLU. The greater the number of ATP molecules present in a sample, greater the RLUs will be detected. Because ATP is an indicator of metabolically active cells, the number of viable cells can be estimated based on the amount of ATP present.

As used herein, the term "therapy" refers to a method, treatment, or composition including, but not limited to, a small or large molecule, a biologic, an immunological cell therapy, radiation, or any other form of medicinal intervention and/or treatment (e.g. ultrasound waves). A therapeutic agent can also be a therapy.

As used herein, the term "therapeutic agent" refers to a composition including, but not limited to small or large molecules, either synthetic or biologic, as well as other forms of medicinal intervention and/or treatment such as ultrasound, proton therapy, or various other forms of radiation, etc. as is known to one of skill in the art.

As used herein, the term "tissue culture" refers to any culture of tissue including two-dimensional (2D) or three-dimensional (3D) cell or tissue culture, with or without additional extracellular matrices, and either directly cultivated from a patient's biopsy or grown in vitro via proliferation techniques including, but not limited to, e.g., organoid growth.

As used herein, the term "treatment effect(s)" refers to a reaction, response, and/or an effect of a therapy, therapeutic agent and the like, for example, on an in vitro or in vivo cell, organoid culture, microtumors, neoplasm, tissues, or a laboratory animal, a volunteer in a clinical trial or a patient. The effects can include, but are not limited to, a sensitivity, resistance, objective tumor response, pathological tumor response, median survival time, progression-free survival, disease-free survival, overall survival, quality of life, etc. as is known to one of skill in the art.

As used herein, the terms "viable," "viable cell(s)" and "cell viability" can be used interchangeably and refer to one or more properties of cells, tissues and organs to maintain or reinitiate a live or survival state. Viability can be quantified and/or observed via the physical properties of cells, tissues and organs, such as mitotic activity in cellular function, contraction of muscle tissue or cells, mechanical activity, metabolic activity, motility and the like. A collection of cells that stop actively growing and dividing/reproducing, for example, following treatment with a cytotoxic compound, can be termed as having a "decrease in cell viability."

Reference will now be made in detail to certain features and embodiments of the disclosed invention, examples of which are illustrated in the accompanying drawings. While the disclosed innovation will be described in conjunction with the enumerated claims, it will be understood that they are not intended to limit those claims. On the contrary, the disclosed innovation is intended to cover all alternatives, modifications, and equivalents, which can be included within the scope of the disclosed invention as defined by the claims.

Disclosed herein are embodiments for assessing or determining effects, including sustaining, cytostatic and/or cytotoxic effects, of therapies, including chemotherapies and/or targeted therapies, on the lifecycle and activity of an organism's tissues and/or cells. The effects can reflect a plurality of cell's (s') lifecycle(s) and cellular activities and the methods can include, but are not limited to, assays measuring the cell's/s' cell death, cell viability, and/or cell proliferation. In one embodiment, the methods utilize the results of a plurality of such assays, e.g. two cell activity assays, using cell lines for which results tend to be highly correlated. However, patient primary cancer tissue comprises a wide range of cell types, so that a live culture of a patient's tumor biopsy may lead to some cells dying while others might not only survive but even grow under the influence of such chemotherapies and targeted therapies. In another embodiment, the methods utilize the results of a plurality of such assays, e.g. two cell activity assays, for patient tumors, for example, in comparison to results of the same or similar assays for one or more cell lines.

A therapy can have more than one actual or potential biological effect. For example, a therapy may result in decreased cell viability and decreased cell proliferation. Alternatively, a therapy may result in only one of decreased cell viability and decreased cell proliferation. The duality of a therapy can have numerous consequences. For example, a goal can be to identify therapies that a) effectively kill tumor cells (cytotoxic effects) and also b) effectively inhibit cell proliferation (cytostatic effects). In such cases, understanding that a potential therapy lacks a cytotoxic and/or cytostatic effect can save valuable time and resources. Generally, assessment of multiple biological effects can be advantageous in determining whether a therapy is meeting the clinically relevant endpoints. Furthermore, a therapy may have both positive and negative biological effects. For example, numerous cytotoxic drug therapeutics have been described that a) effectively kill tumor cell but also b) induce tumor cell proliferation of cancer stem cells (resulting in tumor growth). Therefore, assessing multiple biological effects of a therapy, e.g. determining both the cytotoxic and cytostatic effects, can help to efficiently design, develop, select and effectively administer a cancer therapeutic as well as aid in patient prognosis, patient stratification, and personalized therapeutic development.

The present teachings generally relate to so-called multiplexed methods and kits that are capable of assessing multiple biological effects, e.g., effects on viability and proliferation, on cells, e.g., effects of a potential therapy on tumor cells. More specifically, methods and kits are disclosed that are capable of measuring at least a first and optionally a second detectable marker to simultaneously quantify biological effects, e.g., cell viability and cell proliferation, in a tissue culture, tumor sample, solid cancer, cell culture, malignant cell culture or research cell line, with utility for research, drug development, and patient care.

Viability can be measured by an ATP assay such as CellTiter-Glo® Luminescent Cell Viability Assay, which measures intracellular ATP as an end point or RealTime-GloR MT Cell Viability Assay and CellTiter Fluor Cell Viability Assay (all three from Promega) which are nonlytic assays for measuring cell viability. Cell proliferation can be measured by an EdU assay e.g., "Click-iT EdU Proliferation Assay for Microplates" (Thermo-Fisher) which measures EdU incorporated into replicated DNA after joining an azide group using click chemistry.

In one embodiment, the multiplexed method begins with incubating cells with a glycosylamine and (optionally) treating the cells with a potential therapy such as a therapeutic molecule. The cells can be from an oncology patient. The patient's cells can be from a tumor, a tissue biopsy, a needle aspirate and the like. The cell(s) alternatively be from a research cell line (e.g., Hela cells), as well as growing in vitro in 2-dimensional (2D) and/or three-dimensional (3D) cell models and the like. The glycosylamine as used herein comprises a glycosyl group attached to the amino group of a nucleoside and can be used to measure cell proliferation in either a 2D or 3D tissue culture.

ATP content can be proportional to the number of viable cells (CellTiter-Glo® 3D Cell Viability Assay Technical Manual, Literature #TM412, Revised 1/23, © 2014-2023 Promega Corporation, Madison, WI. U.S.A.). ATP can be measured using a cell viability assay, which uses firefly luciferase to oxidize D-luciferin (with ATP concentration as the rate limiting step) to oxyluciferin and producing and measuring the light (luminescence) emitted to quantify the number of viable cells (Lomakina G. Y., Modestova Y. A., Ugarova N. N., 2015 "Bioluminescence assay for cell viability" Biochemistry Moscow 80, 701-713).

Because ATP is an indicator of metabolically active cells, the number of viable cells can be assessed based on the amount of ATP present. Following glycosylamine incubation the cells can be washed and treated with a permeabilizing agent. Examples of permeabilizing agents include, but are not limited to, Triton X100, digitonin, viroporin, saponin and proteinase K as well as combinations thereof. The principle is to ensure a nearly complete ATP release from the cells into the cell culture medium to quantify the viability with the primary detectable marker while maintaining the cellular structure to quantify proliferation with the second detectable marker in immediate succession. In the disclosed experiments, the inventors used about 2,000 cells/well for quantifying cell viability and cell proliferation. However, the number of cells plated can vary widely, e.g., in previous studies the inventors have observed the possibility of measuring the ATP content with very few cells/well (as low as 10 cells/well). Therefore, less or higher number of cells/well than 2,000 cells can be used.

Multiplexing a measure of viability to quantify cytotoxic effects (sensitivity) while being able to measure anti-proliferative effects to quantify cytostatic effects (resistance) on the same sample provides significant additional insight for primary cancer patient samples because of their inherent poly-clonality. One of the most sensitive and efficient methods to measure the viability of cells (to measure the overall sensitivity of a tissue) is measuring their ATP content using a luciferase-based assay that dissolves the cells so that the ATP can be measured in the supernatant using a luminescent plate reader.

One of the most sensitive and efficient methods to measure the proliferation of cells (i.e., to measure anti-proliferative effects of a sub-clone in response to a treatment of an otherwise sensitive tissue) is measuring the incorporation of a detectable nucleotide analogue instead of thymidine. However, such an assay involves various steps and requires fixed cells that are no longer viable.

ATP content is a reliable measure of cell metabolism and as such a surrogate for cell viability that can be used to quantify the cytotoxicity of anticancer drugs since dead cells have used up all or almost all of their ATP. Thus, while fixed cells are no longer viable one would not expect such cells to contain any meaningful ATP anymore. However, the inventors have looked at various fixation methods and found that in some cases, e.g., with 2% to 4% formalin, almost half of the ATP was still detectable in lysed cells. However, it was not known which factors contributed to that but it is possible that depending on the concentration, duration, and penetration of the fixative, ATPases might have been inhibited to metabolize the ATP, while other enzymes might just not release the ATP as a result of the cross-linking of proteins.

As a next step, it was noticed that after fixation, the cells could be permeabilized, and have almost all of the ATP released into the supernatant, so that measuring of the ATP was accomplished without destroying the cells.

The inventors have hypothesized that this process would enable to first measure the ATP as a measure of viability to quantify cytotoxic effects (i.e. measuring sensitivity of tumor cells to chemotherapies) and subsequently measure a previously incorporated nucleotide analogue e.g., EdU, to quantify anti-proliferative effects (i.e. to measure tumor resistance of subclones to chemotherapy).

Table 1 illustrates the difference between measuring the overall viability of cells vs. the proliferation of cells.

Figure 10:
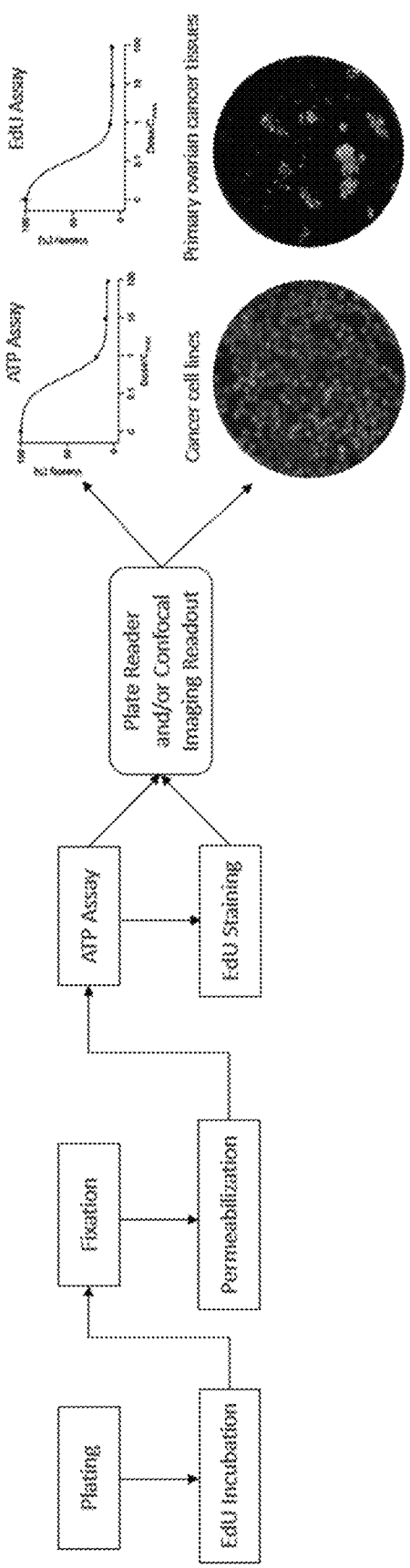
FIG. 10 provides a summary overview of methods according to an embodiment of the invention.

FIG. 10 provides a general overview of an embodiment of the described multiplex assay methods. Cells from a sample are first plated out, for example, using methods as known in the art. EdU is added to the cells and the cells are incubated. The cells are then fixed and permeabilized. After permeabilization, ATP is measured and EdU is detected, for example by staining. Results of the multiplex assay can be assessed by imaging, as shown for a sample of cancer cell lines and a sample of primary ovarian cancer tissues. For each sample, the ATP and EdU results can also or alternatively be assessed by measurement of dose response.

The proposed methods for assaying cell viability and cell proliferation can be performed a) on the same cells and/or sample, b) simultaneously or consecutively, and c) within the same reaction vessel, flask, microtiter well and the like.

The disclosed methods can be performed using an EdU Proliferation Assay in 96-well microtiter plates. Specifically, the disclosed methods can leverage components of the Click-iT™ technology, where EdU is added to live cells and incorporated into DNA during active DNA synthesis to provide a more sensitive assay than the BrdU assay. The presence of a strong alkyne group within EdU can specifically bind to the azide group in fluorochromes, and fluorescence can then be read at specific excitement and emission wavelengths.

In another embodiment, the simultaneous detection of cell viability and proliferation and the quantification of each by measuring the combination of luminescence(s) and/or fluorescence(s) to determine the cell viability and cell proliferation of the same cell culture, can be used in the prediction of treatment effects and efficacy of at least one therapeutic agent on a patient biopsy and/or a cell culture sample in vitro. The patient biopsy can be, for example, from a bone, bone marrow, organ, hard tissue, soft tissue, body fluid, hematological, neurological or cell biopsy and the like. The biopsy can be used to create 3D microtumors or induced to grow as an organoid tissue culture as is known to the skilled artisan. Quantifying via a first detectable marker a decrease in cell viability, e.g., a lower viability for treated cells compared to non-treated cells can be a prediction of sensitivity to the at least one therapeutic agent in vitro and quantifying via a second detectable marker uninhibited cell proliferation for treated cells can predict resistance to the at least one therapeutic agent in vitro.

TABLE 1

|  | Tissue Viability | Tissue Proliferation |
| --- | --- | --- |
| Surrogate Endpoint | Metabolic Activity, e.g. ATP content | DNA synthesis, e.g. incorporation of a nucleotide analogue |
| Being proportional to | the number of viable cells | the number of proliferated cells |
| What it can measure | Can quantify proportion of cells that can be killed by the therapy | Can detect, independent of cell kill, whether a subpopulation is resistant and might grow under supraphysiological concentrations |
| In bacterial testing it would be equivalent to | Cytotoxicity | Cytostatic |
| Clinical relevance | Sensitivity | Resistance |

In a monoclonal cancer cell line, be it a monolayer or a spheroid, there is no cell proliferation when the cells are killed by the substance. However, in a patient, where the drug is cytotoxic for most of the tissue indicting sensitivity, there might be a small number of cells from subclones that would be growing after even the highest concentrations, which could not be detected by the much larger overall cytotoxic effect, and would only be picked up by an independent measurement of true proliferation, which would indicate resistance. In short, when testing drugs/cellular treatment moieties for diseased and non-diseased patient tissues, one can imagine a 2×2 table, one measuring sensitivity (y/n) while the other one resistance (y/n). The identified treatment, whether a single drug, combination of drugs, therapy or therapeutic agent thereof or a combination thereof, would help to verify that the patient receives a single drug, combination of drugs, therapy or therapeutic agent thereof or a combination thereof toward the tumor is more likely than not sensitive rather than resistant.

As indicated above, the present teachings can be implemented in an evaluation of a biological effect of a therapy on cells, e.g., viable cells and viable, malignant cells by assessing both cell viability and cell proliferation. The viable cells can be treated with at least one therapy and a deoxynucleoside. The deoxynucleoside can be labeled as is known to the skilled artisan. Following their treatment, the viable cells can be washed, permeabilized and exposed to first and second detectable markers as described herein. Measuring and detecting, including quantifying, the detectable markers, for cell that are treated vs cells that are not treated, can be indicative of a decline in cell viability following treatment, for example, if a detectable marker's quantity has decreased (e.g. is lower for treated cells compared to untreated cells), and can be indicative of cell proliferation, for example, if a second detectable marker is detected or its quantity is maintained or has increased (e.g. is similar or higher for treated cells compared to non-treated cells).

The methods to quantify detectable markers can be applied in vitro to cells having a relatively fixed location in a sample, for example, cells that exhibit adherence to the cell culture vessel, grow within an extracellular matrix, and/or grow fixed to a surface and/or substrate prior to permeabilization. Furthermore, in any of the methods described herein, the washing of the cells can follow glycosylamine treatment and incubation of the cell culture or can occur after measurement of the first detectable marker. The detectable marker can be one or more of a chemiluminescence marker, bioluminescence marker, a fluorescent dye, a fluorescent label, a radio-label and the like as is known to the skilled artisan. In another embodiment, the first, second and additional detectable markers can be incorporated into a molecule comprising at least one of a nucleoside(s), a nucleotide(s), a nucleoside analog, a nucleotide analog, and the second detectable maker can be for example, but not limited to ethynyl-deoxyuracil (EdU), 5-bromo 2'-deoxyuridine (BrdU), and a molecular analog.

The patient biopsy or research cell (s') response, as seen as a biological effect, to at least one therapeutic agent, treatment, and the like, can foretell one or more of a therapy's and/or treatment's efficacy, patient prognosis, and patient stratification, and can aid in further development, design and refinement of a therapeutic agent, therapeutic testing of new chemotherapies, therapeutic agents, and therapeutic treatments.

Among other things, detecting and/or measuring the combination of luminescence(s) and/or fluorescence(s) to determine the cell viability and cell proliferation on the same cell culture can entail measuring luminescence and/or fluorescence by flow cytometry, confocal microscopy, a plate reader or combinations thereof.

In various embodiments, a kit for determining cell viability and cell proliferation by assaying a sample for viable and proliferating cells is provided. The kit can include at least two detectable markers, wherein the first detectable marker is indicative of and may be used to quantify cell viability, and wherein the second detectable marker is indicative of and may be used to quantify cell proliferation for a single sample, e.g., a plurality of cells, tissue, organ or organoid culture. Quantifying cell viability can be by measuring cellular metabolic activity via the first detectable marker by quantifying cellular metabolic activity by measuring luminescence in a luminescent ATP assay. The first detectable marker can be measured and quantified by at least one of flow cytometry, a plate reader, or a confocal microscope fluorescence imaging, fluorescence spectroscopy, fluorescence microscopy, confocal microscopy, a fluorometer, a fluorescence microplate reader, and fluorescence flow cytometry. The second detectable marker can further include a membrane-permeable dye, fluorescent dye, fluorescent label, a radio-label incorporated into a molecule, e.g., a nucleoside(s), a nucleotide(s), a nucleoside analog and a nucleotide analog during nucleic acid synthesis. The second detectable marker can be at least one of ethynyl-deoxyuracil (EdU), 5-bromo 2'-deoxyuridine (BrdU), 5-Vinyl-2'-deoxyuridine (VdU) and a molecular analog. The kit may include instructions that may direct a user to provide a malignant sample, a patient's biopsy sample, a cell, tissue, organoid or organ sample consisting of isolated and/or specific cells that are determined to be at least one of, e.g., normal, diseased, malignant, or infected cells. The instructions may direct a user to contact the sample with a therapeutic agent, chemotherapy, or any other therapy. The cells may be stained using membrane-permeable fluorescent dyes. The instructions may direct a user to expose the sample under conditions effective to cause emitting of the first detectable marker's luminescence from the one or more viable cells dyed by the first detectable marker. The instructions may direct a user to illuminate the sample under conditions effective to cause emitting of the second detectable marker's fluorescence. In various embodiments, the kit may include instructions to direct the user to conduct any aspect of the methods described herein. The kit may include any aspect of the composition described herein.

The disclosed innovations provide methods and assays that multiplex assays of biological effects, for example proliferation and viability, for example, with measurements using ethynyl deoxy uridine (EdU) inclusion as a marker for proliferation while using adenosine triphosphate (ATP) as a metabolic surrogate marker for viability. Such assays may have mutually exclusive steps. For example, measuring proliferation using the Click-IT EdU assay manufacturer's instructions utilizes fixation and permeabilization steps which kills the cells or tissues, while measuring viability occurs with cells or tissues metabolically active and alive. As demonstrated herein, the disclosed methods nonetheless permit and facilitate assaying of such multiple effects.

Non-Limiting Embodiments of the Invention are Enumerated as Follows:

Embodiment [0001]: Embodiments of the present invention encompass a multiplexed method to assess viability and proliferation of cells from a sample, comprising: incubating a plurality of cells from the sample with a glycosylamine; washing and then permeabilizing said incubated cells; detecting a first detectable marker indicative of viable cells among the plurality of cells; and detecting a second detectable marker indicative of proliferation of a plurality of the viable cells.

Embodiment [0002]: In some embodiments of the present invention, such as, but not limited to, those described in embodiment [0001], the method further comprises: treating a second plurality of cells from the sample with a therapeutic agent; incubating the second plurality of cells from the sample with a glycosylamine; washing and then permeabilizing said treated cells; wherein the first detectable marker is further indicative of viable treated cells among the treated cells; and wherein the second detectable marker is further indicative of proliferation of a plurality of the viable treated cells.

Embodiment [0003]: Embodiments of the present invention encompass a method to evaluate a potential therapeutic agent by detecting cell viability and cell proliferation, comprising: treating viable cells with at least one potential therapeutic agent; incubating the treated cells with a glycosylamine; washing and then permeabilizing the treated and incubated cells; detecting a first detectable marker indicative of viable cells; detecting a second detectable marker indicative of proliferation of the viable cells; wherein efficacy of the potential therapeutic agent is indicated by cell viability and cell proliferation compared to viability and proliferation of cells not treated with the potential therapeutic agent.

Embodiment [0004]: In some embodiments of the present invention, such as, but not limited to, those described in embodiments [0001]-[0003], cell viability indicates cytotoxicity or sensitivity of the therapeutic agent to the cells.

Embodiment [0005]: In some embodiments of the present invention, such as, but not limited to, those described in embodiments [0001]-[0004], cell proliferation indicates cytostaticity or resistance of the cells to the therapeutic agent.

Embodiment [0006]: In some embodiments of the present invention, such as, but not limited to, those described in embodiments [0001]-[0005], the first detectable marker indicates the presence of ATP.

Embodiment [0007]: In some embodiments of the present invention, such as, but not limited to, those described in embodiments [0001]-[0006], the first detectable marker is luciferin.

Embodiment [0008]: In some embodiments of the present invention, such as, but not limited to, those described in embodiments [0001]-[0007], detecting the first detectable marker comprises measuring Relative Luminescence Unit (RLU).

Embodiment [0009]: In some embodiments of the present invention, such as, but not limited to, those described in embodiments [0001]-[0008], the second detectable marker indicates nucleic acid synthesis.

Embodiment [0010]: In some embodiments of the present invention, such as, but not limited to, those described in embodiments [0001]-[0009], the second detectable marker is a glycosylamine or a nucleoside analog.

Embodiment [0011]: In some embodiments of the present invention, such as, but not limited to, those described in embodiments [0001]-[0010], the second detectable marker is ethynyl-deoxyuracil (EdU), 5-bromo 2'-deoxyuridine (BrdU), or 5-Vinyl-2'-deoxyuridine (VdU).

Embodiment [0012]: In some embodiments of the present invention, such as, but not limited to, those described in embodiments [0001]-[0011], the cells comprise cancer cells.

Embodiment [0013]: In some embodiments of the present invention, such as, but not limited to, those described in embodiments [0001]-[0012], the cells are derived from one or more of: a benign tissue, a diseased tissue, an infected tissue, a solid cancer, a hematological cancer and/or combinations thereof.

Embodiment [0014]: In some embodiments of the present invention, such as, but not limited to, those described in embodiments [0001]-[0013], the cells are derived from a 2D cell culture or a 3D cell culture.

Embodiment [0015]: In some embodiments of the present invention, such as, but not limited to, those described in embodiments [0001]-[0014], the cells are derived from at least one of: a tissue culture derived from a cancerous biopsy from a patient; and a tissue culture derived from a non-cancerous biopsy from a patient.

Embodiment [0016]: In some embodiments of the present invention, such as, but not limited to, those described in embodiments [0002]-[0014], the cells are derived from at least one of: a tissue culture derived from a cancer biopsy from a cancer patient undergoing treatment with the potential therapeutic agent; and a tissue culture derived from a non-cancerous biopsy from a cancer patient undergoing treatment with the potential therapeutic agent.

Embodiment [0017]: In some embodiments of the present invention, such as, but not limited to, those described in embodiments [0001]-[0016], washing and then permeabilizing is performed after detecting the second detectable marker and before detecting the first detectable marker.

Embodiment [0018]: In some embodiments of the present invention, such as, but not limited to, those described in embodiments [0001]-[0017], the cells are permeabilized with a permeabilizing agent selected from the group consisting of Triton X100, digitonin, viroporin, saponin, proteinase K, and combinations thereof.

Embodiment [0019]: In some embodiments of the present invention, such as, but not limited to, those described in embodiments [0001]-[0018], the cells are adherent in an extracellular matrix or fixed to a surface prior to permeabilization.

Embodiment [0020]: In some embodiments of the present invention, such as, but not limited to, those described in embodiments [0001]-[0019], the spatial location of the cells is maintained between detecting steps.

Embodiment [0021]: In some embodiments of the present invention, such as, but not limited to, those described in embodiments [0001]-[0020], detecting is by imaging, plate reader, or by flow cytometry.

Embodiment [0022]: In some embodiments of the present invention, such as, but not limited to, those described in embodiment [0021], detecting further comprises quantification.

Embodiment [0023]: In some embodiments of the present invention, such as, but not limited to, those described in embodiments [0002]-[0022], detecting includes determining relative spatial locations of cells that are sensitive or resistant to the potential therapeutic agent.

Embodiment [0024]: In some embodiments of the present invention, such as, but not limited to, those described in embodiments [0001]-[0023], detecting the first detectable marker and detecting the second detectable marker are performed for the same sample of cells or tissue.

Embodiment [0025]: In some embodiments of the present invention, such as, but not limited to, those described in embodiments [0001]-[0024], detecting comprises detecting absorbance(s), luminescence(s) and/or fluorescence(s).

Embodiment [0026]: In some embodiments of the present invention, such as, but not limited to, those described in embodiments [0001]-[0025], the first detectable marker is one or more of: a chemiluminescence marker, bioluminescence marker, fluorescent dye, fluorescent label, and radioactive label.

Embodiment [0027]: In some embodiments of the present invention, such as, but not limited to, those described in embodiments [0001]-[0026], detecting the first detectable marker comprises measuring cellular metabolic activity with an ATP assay.

Embodiment [0028]: In some embodiments of the present invention, such as, but not limited to, those described in embodiments [0001]-[0027], detecting the first detectable marker and/or detecting the second detectable marker comprises measuring color, luminescence or fluorescence of the detectable marker.

Embodiment [0029]: In some embodiments of the present invention, such as, but not limited to, those described in embodiment [0028], color, luminescence or fluorescence is measured by flow cytometry, confocal microscopy, a plate reader, fluorescence imaging, spectroscopy, microscopy or combinations thereof.

Embodiment [0030]: In some embodiments of the present invention, such as, but not limited to, those described in embodiments [0001]-[0029], the second detectable marker is incorporated into a molecule comprising at least one of a nucleoside(s), a nucleotide(s), a nucleoside analog, and a nucleotide analog.

Embodiment [0031]: In some embodiments of the present invention, such as, but not limited to, those described in embodiments [0001]-[0030], the method further comprises identifying a biological effect indicative of one or more of patient prognosis, patient stratification, and efficacy of therapeutic treatments undergoing development.

Embodiment [0032]: Embodiments of the present invention include a kit for determining cell viability and cell proliferation according to any one of embodiments [0001]-[0031], comprising at least two detectable markers, wherein the first detectable marker is indicative of cell viability and the second detectable marker is indicative of cell proliferation.

Embodiment [0033]: In some embodiments of the present invention, such as, but not limited to, those described in embodiment [0032], detection of the first detectable marker is in an ATP luminescent assay measured by flow cytometry, a plate reader, or a confocal microscope Embodiment [0034]: In some embodiments of the present invention, such as, but not limited to, those described in embodiment [0032], detection of the second detectable marker is in an EdU assay quantified by at least one of fluorescence imaging, fluorescence spectroscopy, fluorescence imaging microscopy, epifluorescence microscopy, confocal fluorescence imaging microscopy, a fluorometer, a fluorescence microplate reader, and fluorescence flow cytometry.

EXAMPLES

The invention may be readily understood by reference to the following examples, which are included merely for purposes of illustration of certain aspects and embodiments of the disclosed innovations and are not intended to limit the scope of the innovations in any way.

Example 1: Effect of Paraformaldehyde (PFA) on ATP Measurements

ATP is a water-soluble molecule and is quite stable in solutions between pH 6.8 and 7.4. ATP is highly sensitive to pH and can be rapidly hydrolyzed at extreme pH values. ATP can be quantified using a luminescent luciferin/luciferase reaction calibration curve. Thus, we used relative luminescence units (RLUs) as units to quantify ATP levels, which served as a surrogate for cell viability.

Theoretically, PFA only fixes proteins and should not have any effect on cellular ATP content itself. However, by the virtue of PFA fixing proteins, all enzymes, including those needed to measure cell viability via ATP by luminescence, will be inactivated. If PFA affects measurement of ATP by luminescence, it may need to be washed out before the 3D CellTiter Glo® ATP Luminescent Cell Viability Assay (Catalog No. G9681, Promega, Madison, WI) can be applied to lyse the cells and the luciferase can lead to luminescent emission. An experiment was therefore conducted to see what if any effect PFA had on cellular ATP content and whether it would still be possible to detect ATP in fixed tissue/cells. Four groups of cells were tested:

Group 1 was not pretreated with PFA (control).

Group 2 was treated with 2% PFA.

Group 3 was pretreated with 2% PFA that was then washed out.

Group 4 was pretreated with 4% PFA that was then washed out.

The experiment was conducted as follows. For each group, A549 cells (Catalog No. CCL-185, ATCC, Manassas, VA, USA) were plated in 96-well plates (200 µl/well) with 8 replicates of 1,000 cells in 50 µl cell culture medium per well (DMEM/F12 plus 10% human serum). Cells in group 1, the control group, was not treated with PFA. Cells in groups 2, 3, and 4 were incubated for 15 min. with 2%, 2%, and 4% PFA, respectively. PFA remained in the wells of group 2 and PFA was removed from groups 3 and 4 by washing 3 times with 100 µl Cell culture medium. Luciferase catalyzed ATP luminescence was measured as per CellTiter-Glo 3D manufacturer's instructions.

Luminescence was measured with a BioTek Synergy LX plate reader (Agilent, Santa Clara, CA, U.S.A.) and calculations were performed to quantify, measure, and/or correlate ATP level with cell viability.

We have used a standard (ATP) to gain linear regression standard and calculate the ATP using the standard. We also used relative luminescence unit (RLU) as arbitrary units to calculate ATP level to cell viability.

The results are illustrated in FIG. 1. When 2% or 4% PFA was thoroughly washed out in the groups 3 and 4, ATP luminescence was less than half of the control group. This could be because some of the remaining ATP was "trapped" by denaturalized proteins—for example in mitochondria—or because some of the ATP was released into the extracellular space due to a transient PFA permeabilization of the cell membranes during the fixation.

Example 2: Concentration-Dependent Effect of PFA on ATP Measurements

Based on the previous results the question arose as to which if any PFA concentrations significantly inhibit measurable cellular ATP content. Furthermore, since serum contains proteins, we wanted to know whether incubating and washing with serum could neutralize any potentially residual effect of PFA on ATP measurements. Thus, we created a 4×4 factorial design to expose the cells with 0.0625%, 0.25%, 1%, or 4% of PFA and 0%, 1%, 5%, or 25% of human serum.

For this experiment, A549 cells were plated in 96-well plates with 4 replicates of in 100 µl per well (cell culture medium was DMEM/F12 plus 10% human serum). Cells were fixed with the PFA concentrations for 5 min and washed 3× with phosphate-buffered saline (PBS).

The cells were then incubated at various serum concentrations for 10 min and then washed twice with PBS. Finally, luciferase catalyzed ATP luminescence was measured as per manufacturer's instructions.

Figure 2:
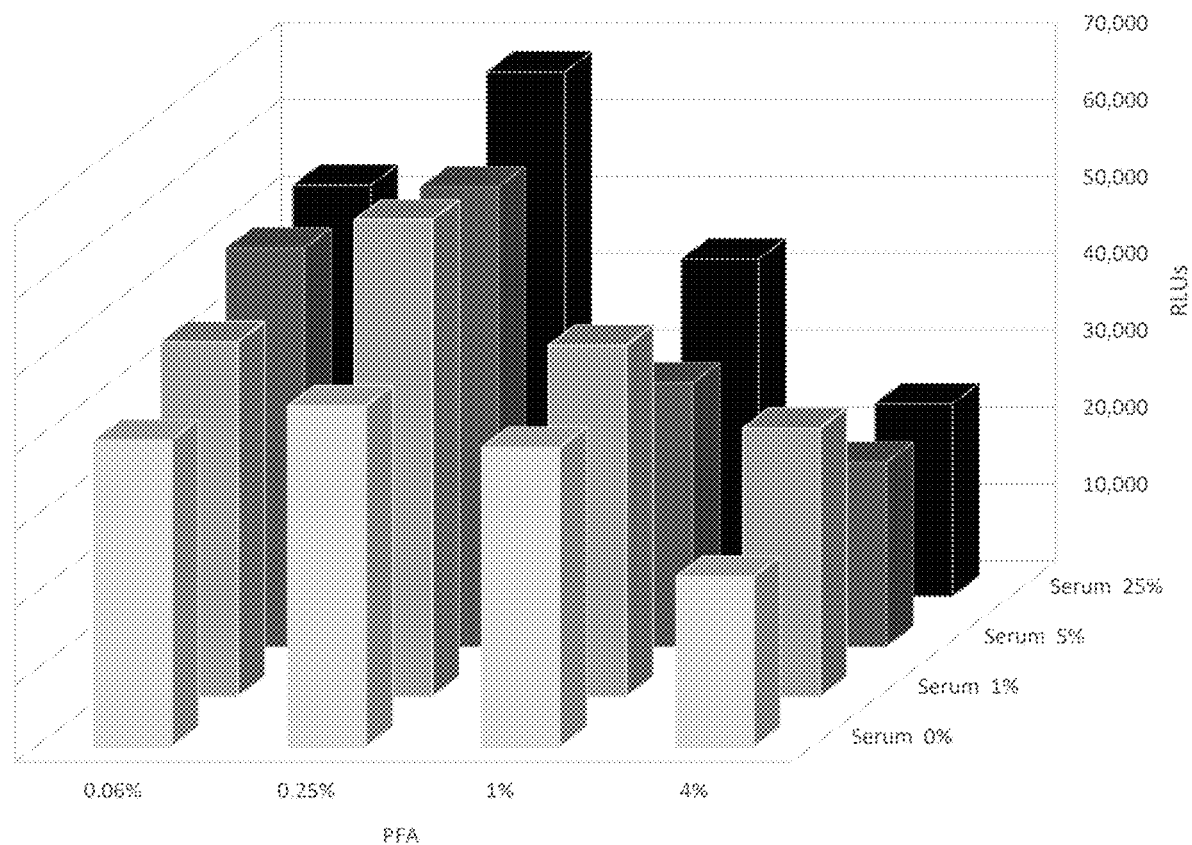
FIG. 2 illustrates the concentrations of PFA, serum and RLU readings, as described in Example 2, to assess concentrations of PFA that inhibit measurable cellular ATP content.

Overall, as shown in Table 2, for a given percentage of serum, RLU was consistently lower for 4% PFA than for lower percentages of PFA. In contrast, for a given percentage of PFA, RLU associated with serum levels (lower RLU being associated with lower serum and higher PFA), though there is significant variability between the groups. The results from Table 2 are illustrated in FIG. 2.

TABLE 2

| | | \multicolumn{5}{c}{Serum} | | | | |
|---|---|---|---|---|---|---|
| | | 0% | 1% | 5% | 25% | Avg. |
| PFA | 4% | 22,097 | 34,860 | 23,912 | 24,987 | 26,464 |
| | 1% | 38,892 | 45,576 | 34,194 | 43,731 | 40,598 |
| | 0.25% | 44,249 | 61,899 | 59,651 | 68,082 | 58,470 |
| | 0.06% | 39,815 | 46,022 | 51,674 | 53,405 | 47,729 |
| | Avg. | 36,263 | 47,089 | 42,358 | 47,551 | 43,315 |

In conclusion, it appears that higher concentrations of PFA-even after having been washed out-reduce the RLU. This may be due to a) proteins capturing some of the ATP or b) residual PFA in the smallest of concentrations affecting the activity of the luciferase. It is not known whether serum itself might buffer some of the potential effect of PFA on the luciferase.

Example 3: Effect of the Presence of PFA on Luciferase Activity

To assess whether the over 50% lower ATP readings after fixation with 2% or 4% PFA are due to fixation blocking the release of ATP or whether residual PFA does inhibit the luciferase activity of the CellTiter-Glo, we measured the RLUs of the CellTiter-Glo as a surrogate for the cellular ATP content before and after the addition of PFA. To better understand whether such a PFA effect might be neutralized by serum we conducted the following analysis. We assessed four groups of A549 cells: with 0.0625% PFA, 0.25% PFA, 1% PFA, and 4% PFA, each of them at 0%, 1%, 5%, or 25% of human serum. For each group, A549 cells were plated in 96 well plates with 4 replicates of 1,000 cells at 100 µl per well. The cell culture medium was DMEM/F12 plus 10% human serum. Luciferase-catalyzed ATP luminescence was then measured using the CellTiter-Glo assay per manufacturer's instructions.

Figure 3:
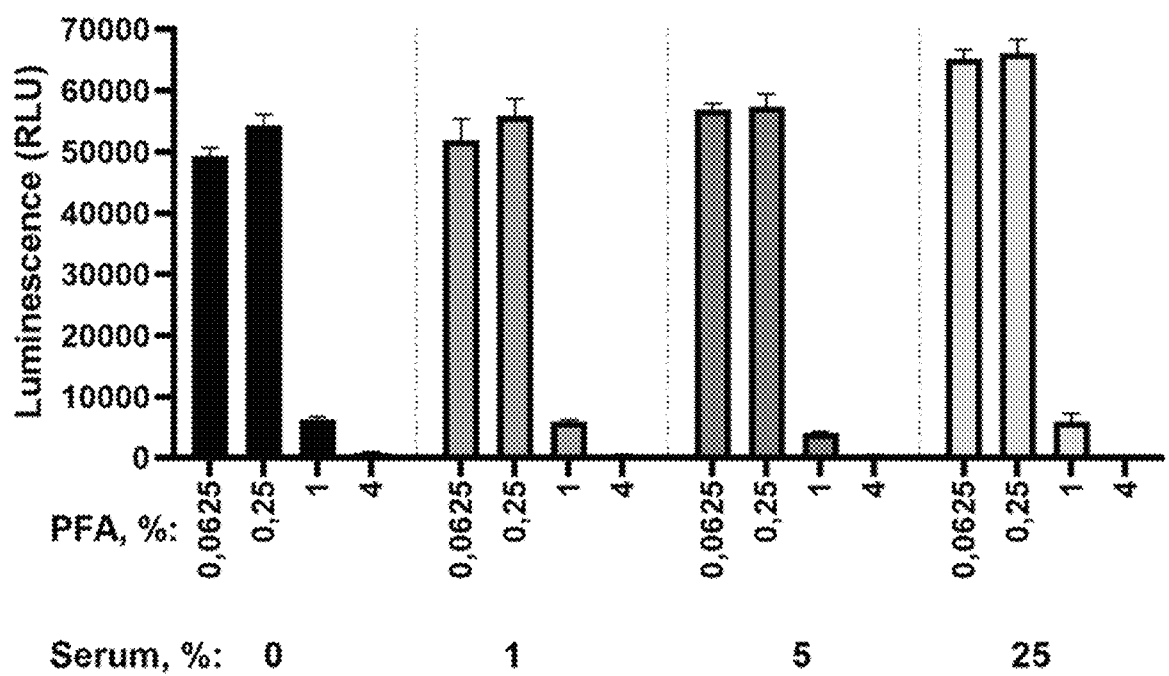
FIG. 3 is a bar graph depicting results for using a combination of PFA and serum in a second round of RLU measurements, as described in Example 3.

A combination of PFA and serum mixture was then created using a 4×4 factorial design of 0.0625%, 0.25%, 1%, or 4% of PFA, and 0%, 1%, 5%, or 25% of human serum, and incubated for 15 min at room temperature. The mixture was then added to the wells and a second round of RLU measurements were taken within 5 min. The results are shown in FIG. 3.

Up to 0.25% PFA added to the CellTiter-Glo solution did not change the RLUs. Thus, it is unlikely that the lower RLUs observed after fixation of the cells and multiple washing with DPBS to remove any residual PFA is due to inhibition of the luciferase.

Furthermore, 1% PFA blocked about 90% of the luciferase activity, while 4% almost completely blocked the luciferase activity. Again, serum seems to slightly increase RLUs but did not seem to neutralize any of the PFA effects.

These results suggest that 2% PFA or more is fixing the cells in a way that only about half of the ATP can be released into the extracellular cell culture medium to be measured as RLUs in the Cell culture medium. In other words, PFA fixation is preventing the release of ATP.

Example 4: Use of a Membrane Permeabilizer to Measure ATP Before PFA Fixation

We considered whether PFA could negatively affect the membrane integrity, which could lead to some ATP leakage that would be washed away during the washing steps to remove PFA. This could be tested with the use of cell membrane permeabilizers that might also be useful to measure ATP before cell fixation.

In a factorial design, the cells were a) treated with 0%, 0.2%, or 1% PFA, and b) treated with or without 0.5% Triton X. ATP was then measured either from the extracellular fluids or within the wells after the use of a cell lysis buffer.

A549 cells were plated in 96 well plates with 4 replicates of 1,000 cells at 100 µl per well. The cell culture medium was DMEM/F12 plus 10% human serum. One out of 3 wells were incubated with 0%, 0.2%, and 1% PFA for 15 minutes and PFA was washed out 3 times with PBS. Half of the wells were then treated with 0.5% Triton X for 10 minutes and the other half received no Triton. The extracellular fluid from half of the 0.5% Triton X treated wells was then transferred to another well-plate and ATP was measured using a luciferin/luciferase complex. The other half of the 0.5% Triton X treated wells were first treated with a lysis buffer and then ATP was measured using the same luciferin/luciferase complex.

Figure 4:
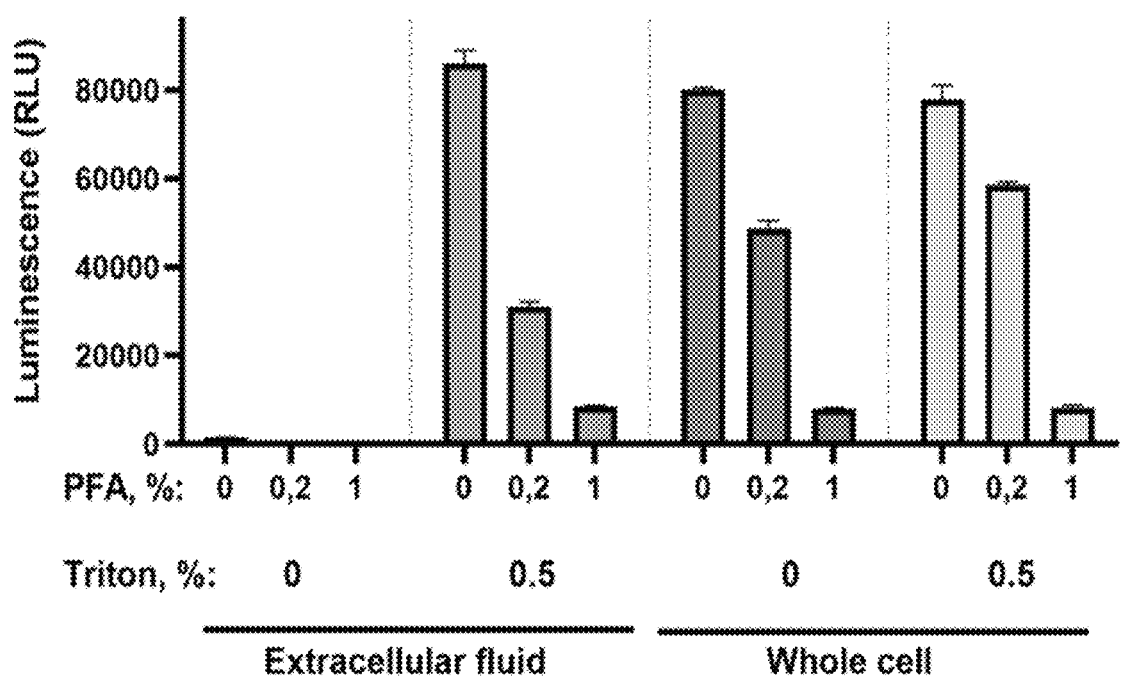
FIG. 4 is a bar graph illustrating the results of Example 4.

The results, shown in FIG. 4, suggest that without Triton X there was no ATP in the extracellular fluid and that neither 0.2% nor 1% PFA lead to some ATP leakage. Triton X alone led to a complete ATP release with similar RLUs as if a lysis buffer were used. However, the ATP released into the extracellular fluid was inhibited in a dose-dependent manner by 0.2% and 1% PFA and the same effect was still present after the use of a cell lysis buffer, suggesting that PFA-induced cellular changes can bind significant amounts of ATP to subcellular structures.

Example 5: SAGE EdU Assay to Detect Viability and Proliferation in A549 and HCT-116 Cells by Confocal Microscopy and Plate Reader We evaluated a number of commercially available EdU kits and modified Lumiprobe's workflow protocol (Lumiprobe Corp., Hunt Valley, Maryland, U.S.A.), using EdU to assay both cell proliferation and DNA replication with Click chemistry using Confocal microscopy and/or Plate Reader for detection and quantification.

For the EdU (5-Ethynyl-2'-deoxyuridine) assays, cells, tissues or organoids are usually fixed with paraformaldehyde (PFA). Since ATP is not a protein, we hypothesized that PFA might not fix or alter ATP and therefore pursued the development of a multiplexed assay to detect cell viability via ATP in fixed tissue/cells. Fluorescence was measured as relative fluorescence units (RFU) to quantify or correlate EdU levels with cell proliferation. Data was analyzed with GraphPad Prism statistical software (GraphPad Software, San Diego, CA, U.S.A.)

Cells were plated into microtiter wells at about 2,000 cells/well and incubated at 37° C. for four days followed by the addition of 10 UM EdU and incubated for another four hours (cell lines, 24 hours for primary cells). If determination of cell sensitivity to a single drug, combination of drugs, therapy or therapeutic agent thereof or a combination thereof was the objective, the drug, combination of drugs, therapy or therapeutic agent(s) would be added 24 hours after plating the cells and remain on the cells for three days prior to EdU incubation. The cell culture medium plus EdU was removed followed by fixation of the cells with PFA for 15 minutes. The cells were washed with PBS and then permeabilized with Triton-X 100 for 30 minutes. The cells were again washed with PBS and then a freshly prepared EdU staining mixture of Copper, azide dye, sodium ascorbate and Tris buffer was added to the cells and incubated for 30 minutes.

The cells were then assayed using Confocal imaging (20×) and via Plate Reader for data acquisition and collection.

The SAGE EdU Assay results are depicted in FIGS. 5A-5E for A549 cells and FIGS. 5F-5J illustrate HCT-116 cells each treated with three concentrations of a single drug, combination of drugs, therapy or therapeutic agent thereof or a combination thereof and compared with two controls, each of the cell lines in cell culture medium (FIGS. 5A and 5F) and in solvent/carrier control (FIGS. 5B and 5G). The number of EdU positive cells decreased with increased concentration of a single drug, combination of drugs, therapy or therapeutic agent thereof or a combination thereof. Pictures were obtained with a confocal microscope at 20×. Hoechst 33342 positive cells were detected in the DAPI channel (blue) and EdU positive cells are detected in the FITC channel (green). Similar results are shown in FIGS. 6A-6G for primary ovarian cells similarly treated and analyzed as in FIG. 5.

Figure 7A:
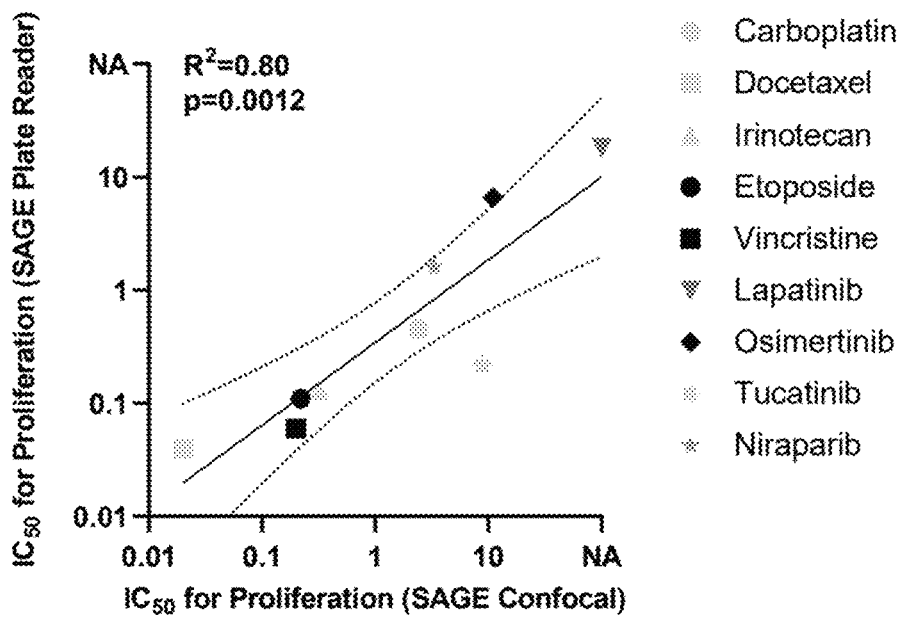
FIG. 7 demonstrates the correlation between results of the SAGE EdU Assay using readouts from the Plate Reader compared to readouts from Confocal Microscopy for A549 (FIG. 7A) and HCT-116 (FIG. 7B) cell lines. Similar correlation values were obtained comparing the Plate Reader with the Confocal Microscopy values for the ATP Assay in A549 cell line (FIG. 7C).
Figure 7B:
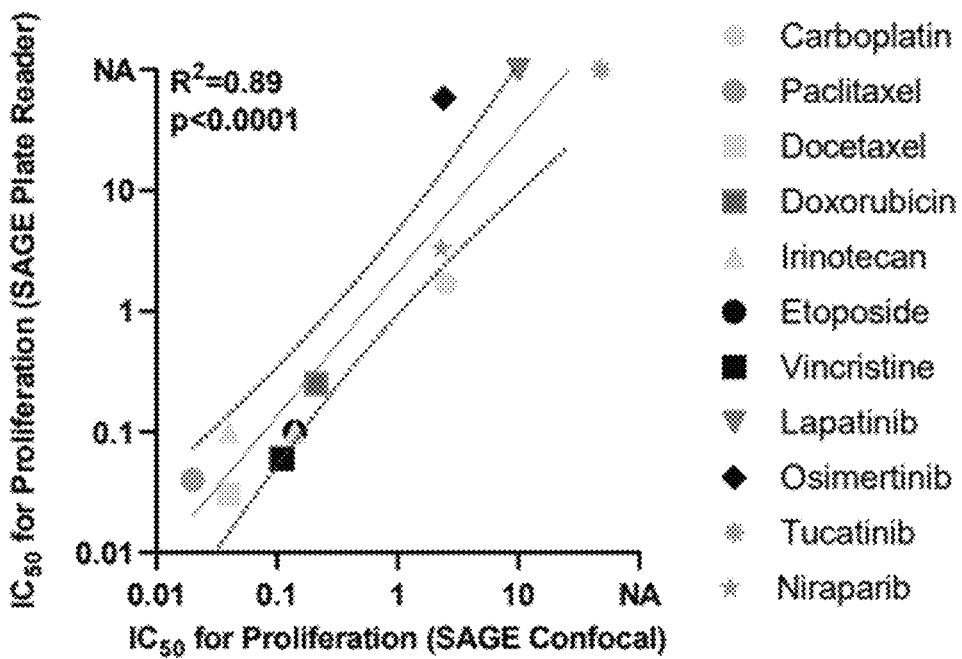
Figures 7, 7C:
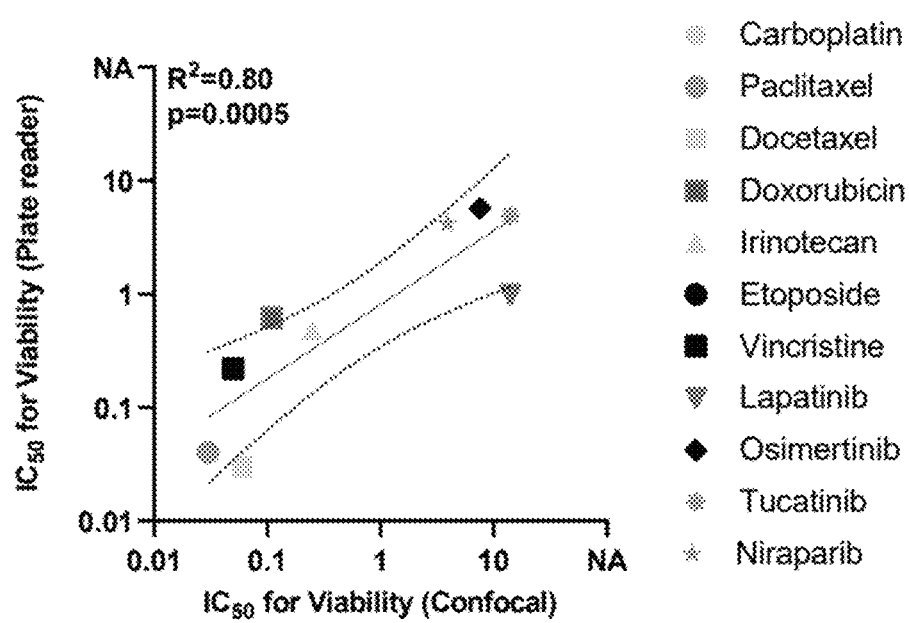

FIG. 7: demonstrates the correlation between results of the SAGE EdU Assay using readouts from the Plate Reader compared to readouts from Confocal Microscopy for A549 cells (FIG. 7A) and HCT-116 cells (FIG. 7B) with the indicated drug, combination of drugs, therapy or therapeutic agent(s). The figures demonstrate that is possible to perform the SAGE EdU Assay using either instrument while obtaining highly correlated and reproducible results. Similar correlation values were also obtained comparing the Plate Reader with the Confocal Microscopy values for the ATP Assay with A549 cells (FIG. 7C). The drug, combination of drugs, therapy or therapeutic agent(s) identified in FIG. 7 and FIG. 8 were used to test the biological effects on cell viability and cell proliferation determined as shown (FIG. 8C and FIG. 8D). The comparison of effects permits identification of potentially efficacious treatments having effects on one or both of viability and proliferation.

Example 6: Correlation Charts SAGE EdU Plate Reader Vs. Confocal Microscope Readouts The majority of commercially available EdU kits are designed for a confocal microscope or a plate reader readout and not for both. As graphically illustrated in FIGS. 7A and 7B, the SAGE EdU Assay readout can be performed similarly well with either a plate reader (PR) instrument or a confocal microscope (CM). The readout of the SAGE EdU assay on both PR and CM correlate the results obtained with a coefficient of correlation that is >0.80.

Example 7: Correlation Charts SAGE EdU Vs. Click-iT EdU

Figure 8A:
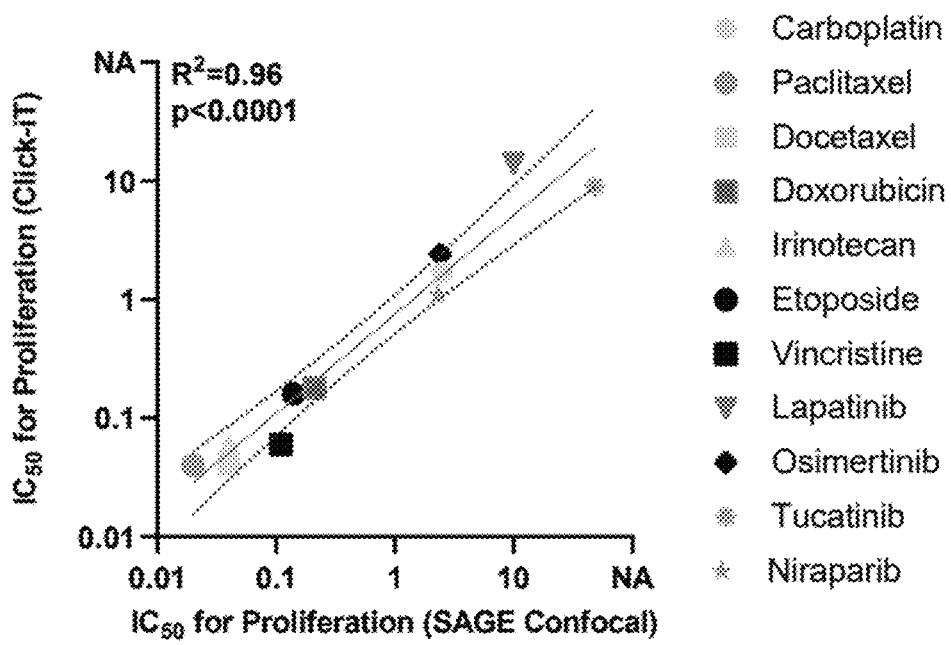
FIG. 8 demonstrates the correlation between results of the SAGE EdU Assay compared to commercially available Click-iT EdU Kit Assays for the HCT-116 cell line using Confocal (FIG. 8A) and Plate Reader (FIG. 8B) readouts.
FIG. 8C (A549 cell line) and 8D (HCT-116 cell line) demonstrate the correlation between the ATP assay performed in the multiplex ATP-EdU Assay plate and in a microtiter plate where only the ATP Assay was performed.
Figure 8B:
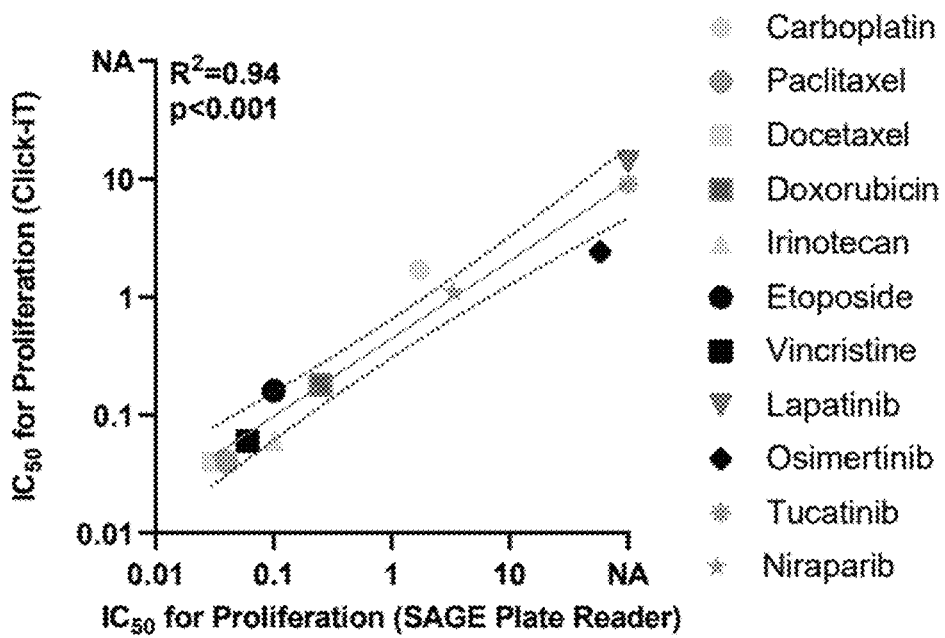
Figure 8:
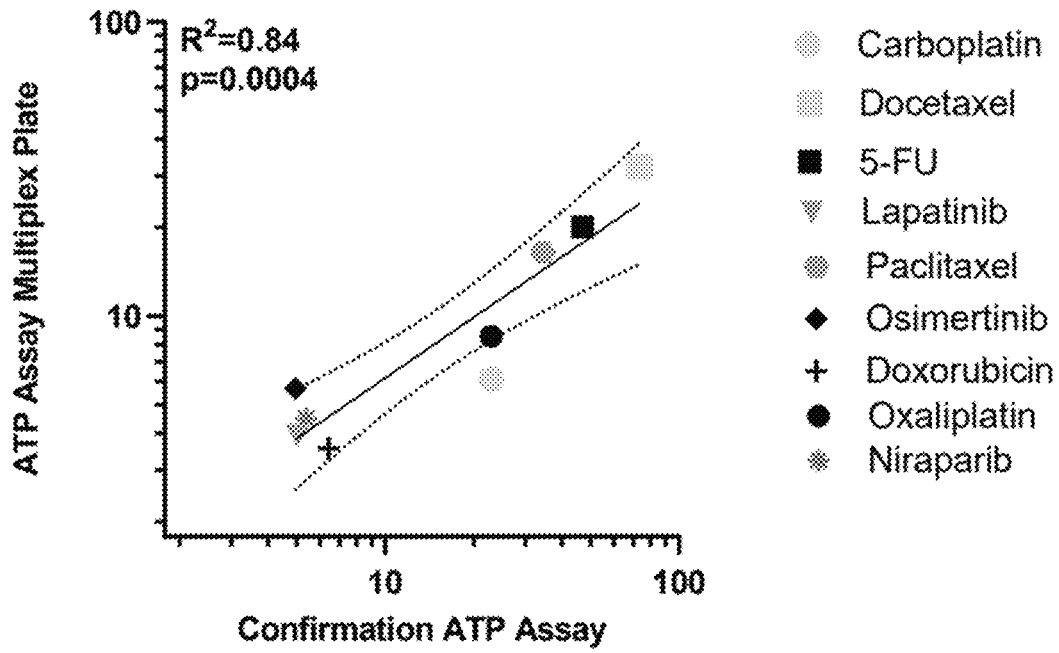
Figure 8:
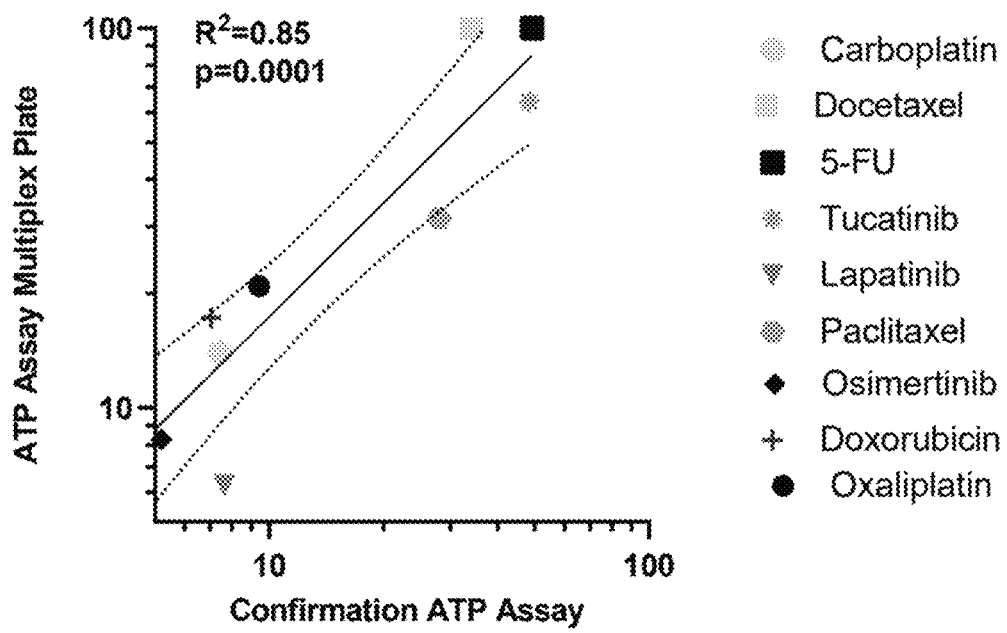

To verify the reliability of the SAGE EdU Assay the same cell lines and primary cells from FIGS. 5 and 6 were evaluated using a commercially available Click-iT EdU Assay Click-iT™ EdU Proliferation Assay for Microplates, Catalog No. C10499, ThermoFisher Scientific, Waltham, Massachusetts, U.S.A. using the same assay conditions. Cells were plated, treated with the drugs listed in FIG. 8, and incubated with EdU. For the SAGE EdU Assay cells were then exposed to a staining mixture composed of copper, a reducing agent and a fluorescent azide in a Tris buffer solution, to allow the click-reaction to occur and the EdU positive cells to be detected. The readout was performed both with the Plate Reader and the Confocal Microscope. The commercial EdU kit (Click-iT EdU Assay from ThermoFisher) was performed per protocol. Data of the SAGE EdU Assay from Plate Reader and Confocal Microscope readouts were compared with the commercial EdU kit using GraphPad Prism. As shown in FIG. 8 there was high correlation between the commercially available EdU kit (Click-iT EdU) with the SAGE EdU assay data. Coefficient of correlation was >0.94 for both as illustrated in FIG. 8A: Click-iT vs SAGE EdU (CM) and FIG. 8B: Click-iT vs SAGE EdU (PR).

Example 8: ATP-EdU Multiplex Assay: Extracellular ATP

It is known that most ATP Assay reagents contain a lysing buffer that facilitates the ATP release from cells causing cellular death. As a result, these reagents are only suitable for endpoint assays. During the development of an assay that multiplexed the ATP and the EdU assay, it was determined to use a non-cellular lysing reagent which allowed quantifying of the cellular ATP as well as permitted simultaneous performance the EdU assay on the same cells.

Figure 11:
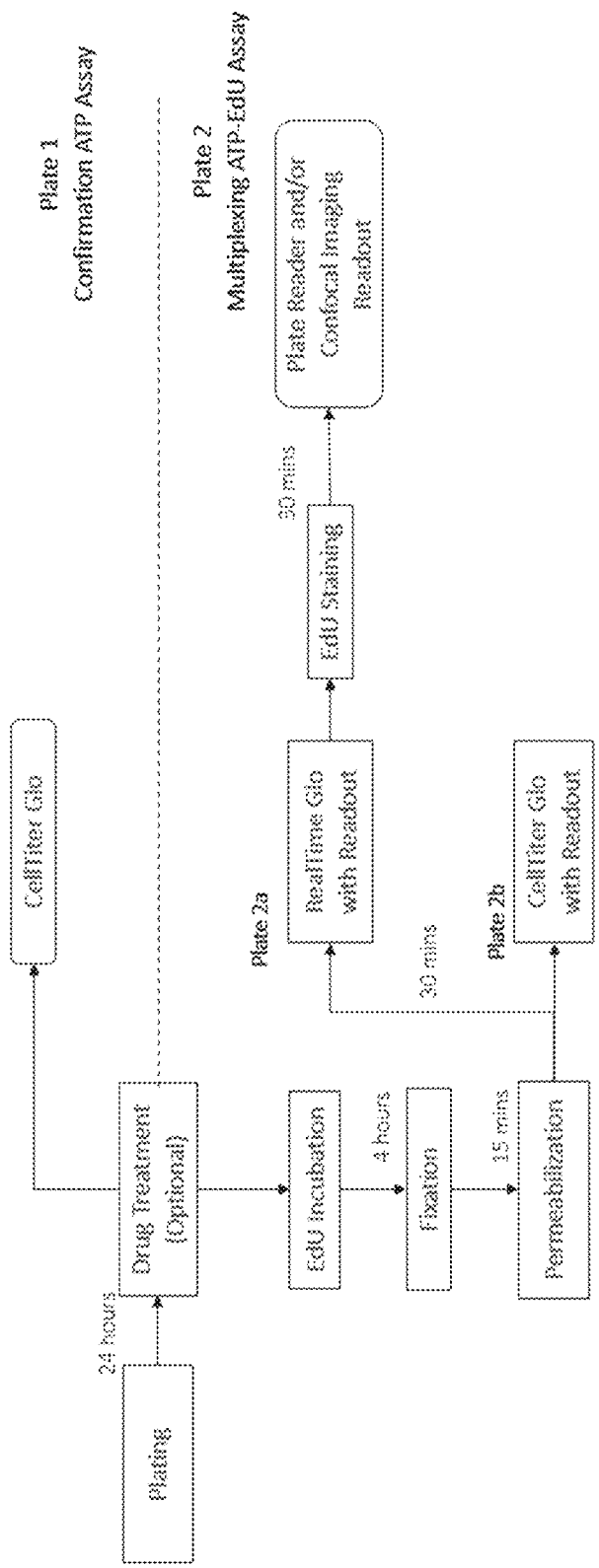
FIG. 11 provides another summary overview of methods according to an embodiment of the invention.

The cells to be evaluated for viability and proliferation were plated and incubated with EdU as described in Example 5. The EdU assay was performed as described in Example 5 with the exception that following the permeabilization step, rather than removing and discarding the supernatant volume from each well, the supernatant was transferred to a new microtiter plate with a multichannel pipette as the ATP within the cells would escape into the supernatant following permeabilization. The ATP transferred from the EdU plate was measured using two reagents, CellTiter Glo® Luminescent Cell Viability Assay (Catalog No. G7570, Promega Corp. Madison, WI, U.S.A.) and RealTime Glo™ MT Cell Viability Assay reagent (Catalog No. G9711, Promega Corp. Madison, WI, U.S.A.) as illustrated in FIG. 11. An additional experiment was conducted demonstrating the possibility of performing the multiplex assay even without moving the cell culture medium into a new plate but measuring the ATP content from the supernatant on the same micro titer plate then after ATP measurement the supernatant was discarded, cells washed and stained with the EdU staining mixture to quantify proliferating cells.

Figure 12:
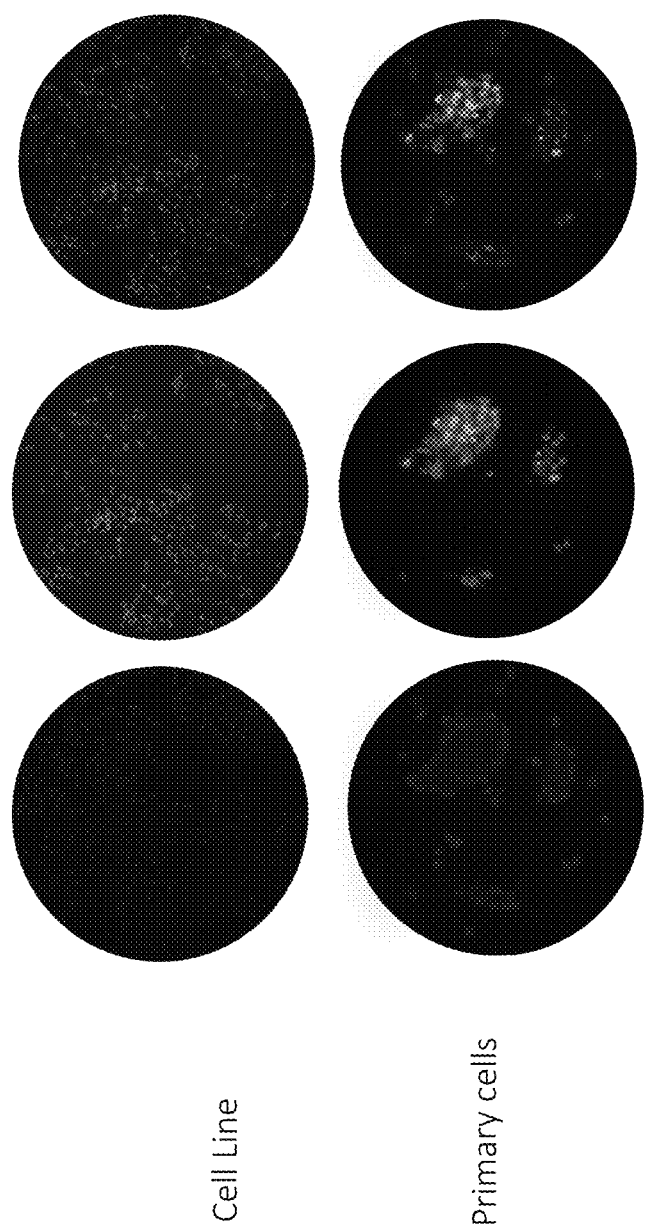
FIG. 12 shows the correspondence of images of cell viability ("Hoechst 33342") with images of cell proliferation ("AF 488 azide"), as demonstrated by the overlay of the images, for each of two sample preparations of cells ("Cell Line" and "Primary Cells"), thus demonstrating the multiplexing potential of the described methods.

FIG. 12 illustrates imaging results for detection of proliferating cells when viability and proliferation tests are performed in a multiplex manner on the same preparation of cells. In this example, the SAGE EdU Assay was performed on HCT-116 cells (a colorectal cancer cell line) at 2,000 cells/well and Primary ovarian cancer cells (25,000 cells/well) with staining with either Hoechst 33342 or AF 488 azide (EdU+ cells) and then an overlay of the two stains to show the bright green cells that are proliferating verse the blue cell that are not actively growing. It is noticed that the primary cells tend to from spheroids and assume a rounded shape. Additionally, the SAGE EdU assay with cell culture medium and staining mixture resulted in the removal of background interference that was problematic with staining mixtures in which copper instability was not factored into the preparation of the staining mixture and inhibited development of a successful ATP/EdU multiplexed assay for cell viability and cell proliferation on the same sample.

FIG. 8C-8D: represents the correlation between the ATP assay performed in the multiplex ATP-EdU Assay plate and a plate where only the ATP Assay was performed. In the multiplexed plate the ATP Assay was performed measuring the extracellular ATP content on permeabilized cells using the RealTime Glo on A549 cells (FIG. 8C) and HCT-116 cells (FIG. 8D). On a separate second plate, the ATP assay was performed using a cell-lysing based reagent (CellTiter Glo). Both ATP reagents were used per protocol. Data were collected using plate reader and compared using GraphPad Prism.

Extremely high correlation was obtained between performing the ATP assay on the permeabilized cells of the EdU plate and the ATP assay performed in a separate plate using the CellTiter Glo reagent (Catalog No. G9681 Promega Corp. Madison, WI, U.S.A). The measurement of the extracellular ATP on the permeabilized cells allowed successfully developing the multiplexed ATP-EdU Assay.

In the multiplex assay viable and proliferating cells are measured consecutively on the same cells: viable cells were detected by measuring the extracellular ATP content whereas proliferating cells were identified performing the SAGE EdU Assay.

Strong correlation of results for ATP assay values were observed when comparing the multiplexing ATP and SAGE EdU assays with the ATP assay conducted using a cell-lysis reagent in a separate plate.

FIG. 9 depicts dose response curves of IC50 values for an ATP assay using a cell-lysing based buffer (FIG. 9A), ATP values of the multiplex plate (FIG. 9B and FIG. 9C) had high correlation with the ATP measurements of a separate plate designated for Confirmation ATP measurements only (FIG. 9A) as shown in the Multiplex workflow in FIG. 11. High correlation was also observed for the SAGE EdU Plate Reader (FIG. 9D) and Confocal Microscope (FIG. 9E) readouts on the multiplex plate.

FIG. 11 illustrates a two-pronged multiplex assay for determining correlation confirmation of a CellTiter Glo ATP assay vs. measuring the ATP from the EdU Assay by extracting the supernatant following cellular permeabilization for ATP assay detection via the RealTime Glo vs. CellTiter Glo ATP assays. The SAGE EdU Assay work flow is used to assess measurement of viability by ATP for multiplex methods vs. non-multiplexed method, for which results are provided in Figure. 9, as discussed above. Data was analyzed with GraphPad Prism statistical software (GraphPad Software, San Diego, CA, U.S.A.).

Thus, Applicants have demonstrated the practicality and efficacy of multiplexing both a cell viability and cell proliferation assay for detecting reduced cell viability, for example, as a predictor of tumor sensitivity, and uninhibited cell proliferation, for example, as a predictor of tumor resistance of malignant cells. The detection or measurement of at least one of cell viability and proliferation can predict the effectiveness of therapy/cellular treatment moiety on cancer cells. The effectiveness can foretell one or more of patient prognosis, patient stratification, and efficacy of therapeutic treatments, including treatments undergoing development.

The disclosure of the present application includes several embodiments, which may share common properties and features. The properties and features of one embodiment may be combined with properties and features of other embodiments. Similarly, a single property or feature or combination of properties or features in any embodiment may constitute a further embodiment.

While the principles of this invention have been described in connection with specific embodiments, it should be understood that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

What is claimed is:

1. A multiplexed high-throughput method to assess viability and proliferation of cells from a cell or tissue sample, comprising:
    a. culturing and incubating cells of the sample with a nucleoside analogue;
    b. washing and then permeabilizing said incubated cells;
    c. detecting viable cells within the sample with a first detectable marker; and
    d. detecting-proliferated cells within the same sample of step c, using a second detectable marker,
    wherein the first detectable marker comprises ATP as a surrogate for cellular metabolism indicating viability;
    wherein the second detectable marker is selected from the group consisting of: ethynyl-deoxyuracil (EdU), 5-bromo 2'-deoxyuridine (BrdU), 5-Vinyl-2'-deoxyuridine (VdU), indicating cell proliferation through nucleic acid synthesis; and
    wherein the measurement of the second detectable marker is not affected by the measurements of the first detectable marker, and vice versa.

2. The method of claim 1, further comprising culturing and incubating cells of the sample with a therapeutic agent before or during step 1a.

3. The method of claim 2, further comprising determining at least one treatment effect based on a measurement of one or both detectable markers.

4. The method of claim 3, wherein determining a treatment effect is relative to:
    a) standard, and/or
    b) cells of the sample that were not treated with the therapeutic agent.

5. The method of claim 3, where the sample comprises malignant cells and a treatment effect on viable cells is a measure of cytotoxicity predicting tumor sensitivity in a cancer patient; or
    a treatment effect on proliferation is a measure of cytostaticity predicting tumor resistance in a cancer patient.

6. The method of claim 2, wherein the cells are derived from one or more of: a benign tissue, a diseased tissue, an infected tissue, a solid cancer, and a hematological cancer.

7. The method of claim 2, wherein the cells are derived from at least one of:
    a tissue culture derived from a cancer biopsy from a cancer patient undergoing treatment with the potential therapeutic agent; and
    a tissue culture derived from a non-cancerous biopsy from a cancer patient undergoing treatment with the potential therapeutic agent.

8. The method of claim 1, wherein washing and then permeabilizing is performed after detecting the second detectable marker and before detecting the first detectable marker.

9. The method of claim 1, wherein the cells are permeabilized with a permeabilizing agent selected from the group consisting of octyl phenol ethoxylate, digitonin, viroporin, saponin, proteinase K, and combinations thereof.

10. The method of claim 1, wherein the cells are adherent in an extracellular matrix or fixed to a surface prior to permeabilization.

11. The method of claim 1, wherein detecting is by at least one of imaging, plate reader, flow cytometry, confocal microscopy, fluorescence imaging, spectroscopy, and microscopy, and measuring comprises at least one of luminescence(s), fluorescence(s), absorbance(s) and radiation.

12. The method of claim 1, wherein detecting further comprises quantification.

13. The method of claim 1, wherein detecting includes determining relative spatial locations of cells that are sensitive or resistant to the potential therapeutic agent.

14. The method of claim 1, wherein the first detectable marker is one or more of: a luminescence marker, fluorescent label, absorbant label and radioactive label.

15. The method of claim 1, further comprising identifying a biological effect indicative of one or more of patient prognosis, patient stratification, and efficacy of therapeutic treatments undergoing development.

16. A multiplexed high-throughput method to assess viability and proliferation of cells from a cell or tissue sample, comprising:

a. culturing and incubating cells of the sample with a nucleoside analogue;
   b. washing and then permeabilizing said incubated cells;
   c. detecting viable cells within the sample with a first detectable marker that quantifies metabolic activities; and
   d. detecting proliferated cells within the same sample of step c, using a second detectable marker,
wherein the first detectable marker comprises ATP as a surrogate for cellular metabolism indicating viability;
wherein the second detectable marker is selected from the group consisting of: ethynyl-deoxyuracil (EdU), 5-bromo 2'-deoxyuridine (BrdU), 5-Vinyl-2'-deoxyuridine (VdU), indicating cell proliferation through nucleic acid synthesis; and
wherein the measurement of the second detectable marker is not affected by the measurements of the first detectable marker, and vice versa.

\* \* \* \* \*